(12) United States Patent
Taylor

(10) Patent No.: US 10,167,320 B2
(45) Date of Patent: Jan. 1, 2019

(54) PURIFICATION OF VIRUS LIKE PARTICLES

(71) Applicant: Takeda Vaccines, Inc., Cambridge, MA (US)

(72) Inventor: Ross Taylor, Cambridge, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 641 days.

(21) Appl. No.: 13/925,449

(22) Filed: Jun. 24, 2013

(65) Prior Publication Data

US 2014/0004145 A1   Jan. 2, 2014

Related U.S. Application Data

(60) Provisional application No. 61/794,086, filed on Mar. 15, 2013, provisional application No. 61/663,218, filed on Jun. 22, 2012.

(51) Int. Cl.
   *C07K 14/005* (2006.01)
   *C12N 7/00* (2006.01)

(52) U.S. Cl.
   CPC .......... *C07K 14/005* (2013.01); *C12N 7/00* (2013.01); *C12N 2710/14143* (2013.01); *C12N 2770/16022* (2013.01); *C12N 2770/16023* (2013.01); *C12N 2770/16051* (2013.01)

(58) Field of Classification Search
   None
   See application file for complete search history.

(56) References Cited

U.S. PATENT DOCUMENTS

| | | |
|---|---|---|
| 5,641,870 A | 6/1997 | Rinderknecht et al. |
| 6,415,945 B1 | 7/2002 | McCarthy et al. |
| 6,416,945 B1 | 7/2002 | McCarthy et al. |
| 6,565,905 B1 | 5/2003 | Ito et al. |
| 6,602,697 B1 | 8/2003 | Cook |
| 7,041,500 B2 | 5/2006 | Robinson |
| 7,067,638 B1 | 6/2006 | Takeda et al. |
| 7,481,997 B1 | 1/2009 | Hardy |
| 7,527,801 B2 | 5/2009 | Coit et al. |
| 7,575,753 B2 | 8/2009 | Takeda et al. |
| 7,879,338 B2 | 2/2011 | Hamilton et al. |
| 7,955,603 B2 | 6/2011 | Richardson et al. |
| 8,067,560 B2 | 11/2011 | Takeda et al. |
| 8,119,145 B2 | 2/2012 | Coit et al. |
| 8,124,104 B2 | 2/2012 | Coit et al. |
| 8,277,819 B2 | 10/2012 | Jiang et al. |
| 8,357,792 B2 | 1/2013 | Takeda et al. |
| 8,431,116 B2 | 4/2013 | Richardson et al. |
| 8,481,693 B2 | 7/2013 | Vedvick et al. |
| 8,841,120 B2 | 9/2014 | Richardson et al. |
| 8,980,275 B2 | 3/2015 | Steadman et al. |
| 9,272,028 B2 | 3/2016 | Richardson et al. |
| 9,308,249 B2 | 4/2016 | Richardson et al. |
| 9,359,410 B2 | 6/2016 | Vedvick et al. |
| 9,518,096 B2 | 12/2016 | Richardson et al. |
| 2001/0033837 A1 | 10/2001 | Metzner et al. |
| 2004/0063188 A1 | 4/2004 | Robinson et al. |
| 2007/0207526 A1 | 9/2007 | Coit et al. |
| 2010/0150961 A1 | 6/2010 | Vedvick et al. |
| 2012/0141529 A1 | 6/2012 | Coit et al. |
| 2012/0156243 A1 | 6/2012 | Richardson et al. |
| 2013/0344107 A1 | 12/2013 | Vedvick et al. |
| 2014/0004145 A1 | 1/2014 | Taylor |
| 2016/0317645 A1 | 11/2016 | Vedvick et al. |

FOREIGN PATENT DOCUMENTS

| | | |
|---|---|---|
| CN | 102260651 A | 11/2011 |
| JP | H03-243861 A | 10/1991 |
| JP | 10-500847 | 1/1998 |
| JP | 2003-066021 A | 3/2003 |
| WO | WO9615247 | 5/1996 |
| WO | WO 1999/061475 A1 | 12/1999 |
| WO | WO 2003/102132 A2 | 12/2003 |
| WO | WO 2004/020971 A2 | 3/2004 |
| WO | WO 2005/032457 A2 | 4/2005 |
| WO | WO 2006/136566 | 12/2006 |
| WO | WO 2006/138514 A2 | 12/2006 |
| WO | WO 2008/113011 | 9/2008 |
| WO | WO 2009/080781 A1 | 7/2009 |
| WO | WO 2011/012726 A2 | 2/2011 |
| WO | WO 2012/040216 A1 | 3/2012 |
| WO | WO 2013/192604 | 12/2013 |

OTHER PUBLICATIONS

Almanza et al., Self-Assembly of the Recombinant Capsid Protein of a Swine Norovirus into Virus-Like Particles and Evaluation of Monoclonal Antibodies Cross-Reactive with a Human Strain from Genogroup II, 2008, Journal of Clinical Microbiology, vol. 46, No. 12, pp. 3971-3979.*
Communcation for European Application No. 08782762 dated Aug. 12, 2011.
Communcation for European Application No. 08782762 dated Mar. 30, 2012.
Decision to grant Patent in corresponding Japanese Application No. JP2009553820 dated Apr. 30, 2013.
Examination Report No. 1 in corresponding Australian Application No. 2008-224877 dated Jun. 25, 2012.
SITCH Extended European Search Report for European Application No. 08782762 dated Jul. 26, 2011.
YOUNG International Search Report and Written Opinion for International Application No. PCT/US2008/57072 dated Oct. 1, 2008.
International Search Report PCT /US13/47249 dated Nov. 14, 2013.
Notice of Acceptance in corresponding Australian Application No. 2008-224877 dated Jul. 2, 2013.
Office Action in corresponding European Application No. 08782762 dated Mar. 25, 2014.

(Continued)

*Primary Examiner* — Benjamin P Blumel
(74) *Attorney, Agent, or Firm* — Cooley LLP

(57) ABSTRACT

Methods of purifying virus-like particles (VLPs) that are substantially free of process contaminants and infectious agents. The methods incorporate, for example, low-pH treatment during harvest and/or inactivation by a solvent and/or detergent during VLP capture.

9 Claims, 4 Drawing Sheets

(56) References Cited

OTHER PUBLICATIONS

Office Action in corresponding Japanese Application No. 2009553820 dated Jan. 7, 2013.
Office Action for U.S. Appl. No. 12/531,248 dated Jan. 31, 2012.
Ausar,et al., "Conformational stability and disassembly of norwalk virus like particles: effect of pH and temperature," Bioi. Chem. 281:19478-19488 (2006).
Ball et al. "Oral Immunization with Recombinant Norwalk Virus-Like Particles Induces a Systemic and Mucosal Immune Response in Mice," Journal of Virology 72:1345-1353 (1998).
Ball et al., Recombinant Norwalk virus-like particles given orally to volunteers: phase I study. Gastroenterology 117:40-48 (1999).
Baric et al., "Expression and self-assembly of Norwalk virus capsid protein from venezuelan equine encephalitis virus replicons," J. Virol. 76(6):3023-3030 (2002).
Bertolotti-Ciarlet et al., "Structural requirements for the assembly of Norwalk virus-like particles," J. Virol. 76(8):4044-4055 (2002).
Cao, et al., "Structural basis for the recognition of blood group trisaccharides by norovirus," J. Virol. 81(11):5949-5957 (2007).
Chen et al.., "X-ray structure of a native calicivirus: structural insights into antigenic diversity and host specificity," Proc. Natl Acad. Sci. USA 103(21):8048-8053 (2006).
Cook et al., "Purification of virus-like particles ofrecombinant human papillomavirus type II major capsid protein L I from *Saccharomyces cerevisiae*," Protein Expr. Purif. 17(3):477-484 (1999).
Estes et al., "Norwalk Virus Vaccines: Challenges and Progress," The Journal of Infectious Disease 181(Suppl2):S367-373 (2000).
Fankhauser et al., "Molecular epidemiology of 'Norwalk-like viruses' in outbreaks of gastroenteritis in the United States," J. Infect. Dis. 178(6):1571-1578 (1998).
Herbst-Kralovetz, et al., "Norwalk virus-like particles as vaccines," Expert Rev. Vaccines 9(3): 299-307 (2010).
Jiang et al., "Expression, self-assembly, and antigenicity of the Norwalk virus capsid protein," J. Viral. 66(11):6527-6532 (1992).
Jiang et al, "Norwalk virus genome cloning and characterization,"Science, 250:1580-1583 (1990).
Mason et al., "Expression of Norwalk virus capsid protein in transgenic tobacco and potato and its oral immunogenicity in mice," Proc. Nat! A cad. Sci. USA 93(11):5335-5340 (1996).
Nicollier-Jamot et al. Vaccine 22:1079-1086 (2004).
Oka et al., "Expression of sapovirus virus-like particles in mammalian cells," Arch. Virol., 151:399-404 (2006).
Pattenden et al., "Towards the preparative and large-scale precision manufacture of virus-like particles," Trends Biotechnol. 23(10): 523-529 (2005).
Prasad et al., "Structural studies of recombinant norwalk caps ids," J. Infect. Dis. 181 (52):S317-S321 (2000).
Rolland et al., "Purification of recombinant HBc antigen expressed in *Escherichia coli* and Pichia pastoris: comparison of size-exclusion chromatography and ultracentrifugation," J. Chromatog. B Biomed. Sci. App. 753(1): 51-65 (2001).
Antiseptics and Disinfectants for Infection Control, vol. 11, No. 1, pp. 28-31 (May 20, 2004).
Huhti L. et al. "A comparison of methods for purification and concentration of norovirus GII-4 capsid virus-like particles." *Archives of Virology* 155 (11) 1855-1858. Aug. 19, 2010.
Koho Tiia et al. "Purification of norovirus-like particles (VLPs) by ion exchange chromatography." *Journal of Virological Methods* 181(1) 6-11. Jan. 5, 2012.
Lai, Huafang and Chen, Qiang. "Bioprocessing of plant-derived virus-like particles of Norwalk virus capsid protein under current Good Manufacture Practice regulations." Plant Cell Rep. 31(3) 573-584. Dec. 2, 2011.
Parra, G. et al. "Immunogenicity and specificity of norovirus Consensus GII.4 virus-like particles in monovalent and bivalent vaccine formulations." *Vaccine* 30(24) 3580-3586. Mar. 19, 2012.
Extended European Search Report, EP13807804.3, dated Nov. 3, 2015.
Nakata, S. "Calicivirus." *Viruses* vol. 52, No. 1, pp. 7-13 (Jun. 1, 2002).

Nakata, Shuji "Vaccine development for Norwalk Virus." *Nippon Rinsho*, vol. 60, No. 6, pp. 1222-1227 (Jun. 1, 2002).
Nagesha et al. "Self-assembly, antigenicity, and immunogenicity of the rabbit haemorrhagic disease virus (Czechoslovakian strain V-351) capsid protein expressed in baculovirus." *Arch Virol*, vol. 140, No. 6, pp. 1095-1108 (Jun. 21, 1995).
Xia et al. "Norovirus Capsid Protein Expressed in Yeast Forms Virus-Like Particles and Stimulates Systemic and Mucosal Immunity in Mice Following an oral Administraiton of Raw Yeast Extracts." *J. Med Virol.*, vol. 79, No. 1, pp. 74-83 (Jan. 2007).
Taube et al. "Generation of recombinant Norovirus-like particles (VLP) in the human endothelial kidney cell line 293T." *Arch Virol.*, vol. 150, No. 7, pp. 1425-1431 (Jul. 2005).
Kobayashi and Sumi. "Infectious Viral Enteritis." *Igaku no Ayumi*, vol. 218, No. 10, pp. 868-876 (Sep. 2, 2006).
Extended European Search Report for EP Application No. 13807804.3 dated Nov. 3, 2015. 8 pages.
Huafang Lai et al. "Bioprocessing of plant-derived virus-like particles of Norwalk virus capsid protein under current Good Manufacture Practice regulations." *Plant Cell Reports* 31 (3): 573-584. Dec. 2, 2011.
Parra et al. "Immunogenicity and specificity of Norovirus consensus GII.4 virus-like particles in monovalent and bivalent vaccine formulations." *Vaccine* 30(24):3580-3586. Mar. 19, 2012.
International Preliminary Report on Patentability for International Application No. PCT/US2013/047249, dated Dec. 23, 2014, 15 pages.
International Search Report and Written Opinion for International Application No. PCT/US2013/047249, dated Nov. 14, 2013, 16 pages.
Chen, Q. "Expression and purification of pharmaceutical proteins in plants." Biol Eng (2008); 1.4: 291-321.
Peixoto, C., et al. "Downstream processing of triple layered rotavirus like particles." Journal of Biotechnology (2007); 127.3: 452-461.
Australian Patent Application No. 2008224877, Second Examination Report dated May 21, 2013, 2 pages.
Australian Patent Application No. 2013242822, Examination Report dated Aug. 27, 2015, 3 pages.
Australian Patent Application No. 2016269506, Examination Report dated Jan. 10, 2018, 4 pages.
Canadian Patent Application No. 2,683,977, Office Action dated Aug. 14, 2014, 4 pages.
Canadian Patent Application No. 2,683,977, Office Action dated Jul. 20, 2015, 3 pages.
Chapter 2: Methods for Purification of Proteins, 4. Purification by Column Chromatography, Separate Volume of Experimental Medicine: Protein Experiment Handbook—Summary of basic mechanisms and latest protocols on separation/purification, mass spectrometry, antibody preparation and molecular interaction analysis, Yodosha Co., Ltd., 2006, pp. 32-46 (Non English document); 16 pages.
Chapter 4: Methods for Separation and Purification, Perfect Biotechnical Series, Notebook for Protein Experiment, Part I: Extraction and Separation/purification, Yodosha Co., Ltd., 1998, pp. 71-76 (Non English document); 7 pages.
Chinese Patent Application No. 201380043618.X, Office Action and Search Report dated Apr. 27, 2016, with English translation, 18 pages.
Chinese Patent Application No. 201380043618.X, Office Action dated Sep. 27, 2017, with English translation, 14 pages.
Chinese Patent Application No. 201380043618.X, Office Action dated Mar. 22, 2017, with English translation, 14 pages.
European Patent Application No. 13807804.3, Examination Report dated Feb. 5, 2018, 5 pages.
Japanese Patent Application No. 2013-112580, Office Action dated Aug. 23, 2016, with English translation, 11 pages.
Japanese Patent Application No. 2013-112580, Office Action dated Oct. 21, 2014, with English translation, 6 pages.
Japanese Patent Application No. 2015-518633, Office Action dated Mar. 28, 2017, with English translation, 18 pages.
Japanese Patent Application No. 2015-518633, Office Action dated Jan. 31, 2018, with English translation, 27 pages.

(56) References Cited

OTHER PUBLICATIONS

Japanese Patent Application No. 2017-032171, Office Action dated Dec. 22, 2017, and English translation, 11 pages.
Korean Patent Application No. 10-2009-7021421, Office Action dated Apr. 27, 2015, with English translation, 9 pages.
Korean Patent Application No. 10-2009-7021421, Office Action dated Sep. 29, 2014, with English translation, 13 pages.
Korean Patent Application No. 10-2015-7020558, Office Action dated Feb. 13, 2017, with English translation, 7 pages.
Korean Patent Application No. 10-2015-7020558, Office Action dated Sep. 22, 2016, with English translation, 6 pages.
Korean Patent Application No. 10-2015-7020558, Office Action dated Nov. 4, 2015, with English translation, 7 pages.
Korean Patent Application No. 10-2016-7036031, Office Action dated Feb. 13, 2017, with English translation, 9 pages.
Mexican Patent Application No. MX/a/2014/015842, Office Action dated Aug. 14, 2017, 4 pages. (Non-English document with cited references in English).
Mexican Patent Application No. MX/a/2014/015842, Office Action dated Jan. 16, 2018, 8 pages. (Non-English document with cited references in English).
Pakistani Patent Application No. 423/2013, Office Action dated Jun. 24, 2016, 1 page.
Taiwanese Patent Application No. 102122276, Office Action dated Aug. 30, 2017, with English translation, 7 pages.
U.S. Appl. No. 12/531,248, Office Action dated Aug. 20, 2012, 10 pages.
U.S. Appl. No. 13/914,331, Office Action dated Apr. 27, 2015, 5 pages.
U.S. App. No. 13/914,331, Office Action dated Aug. 14, 2015, 5 pages.
U.S. Appl. No. 15/144,265, Office Action dated Apr. 18, 2018, 10 pages.
U.S. Appl. No. 15/144,265, Office Action dated Oct. 19, 2017, 9 pages.
Australian Patent Application No. 2013277959, Examination Report dated May 1, 2018, 16 pages.
Dika, et al., "Impact of Internal RNA on Aggregation and Electrokinetics of Viruses: Comparison between MS2 Phage and Corresponding Virus-Like Particles." Appl. Environ. Microbiol. (2011); 77 (14): 4939-4948.
Vicente, et al., "Large-scale production and purification of VLP-based vaccines." Journal of Invertebrate Pathology (2011); 107: S42-S48.
Mexican Patent Application No. MX/a/2014/015842, Office Action dated Aug. 21, 2018 (dated Sep. 21, 2018), 6 pages. (Non English document with cited references in English).

\* cited by examiner

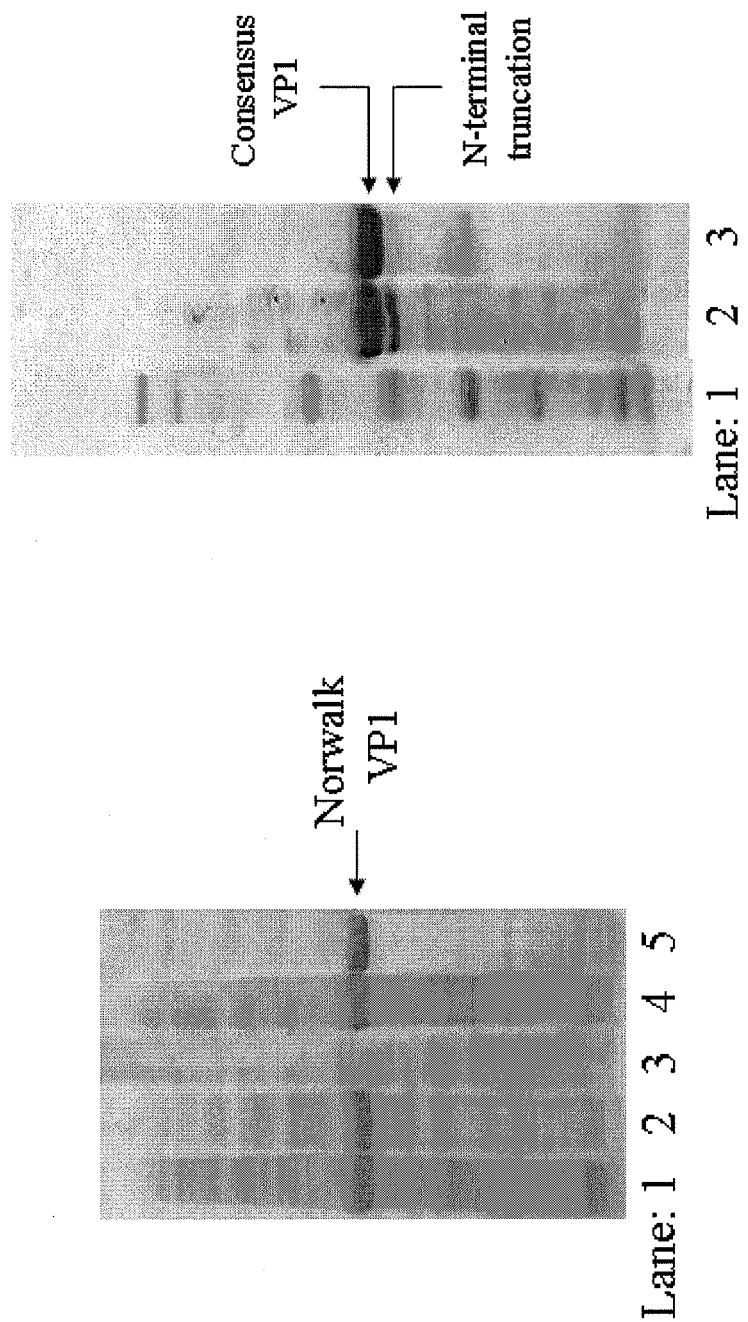

PURIFICATION OF VIRUS LIKE PARTICLES

CROSS-REFERENCE TO RELATED APPLICATIONS

This application claims priority to U.S. Provisional Patent Application No. 61/663,218, filed Jun. 22, 2012, and U.S. Provisional Patent Application No. 61/794,086, filed Mar. 15, 2013, the entire contents of each of which is incorporated herein by reference in its entirety.

FIELD OF THE INVENTION

The invention is in the field of vaccines, including vaccines for noroviruses. Aspects of the invention relate to methods of preparing and purifying vaccine compositions.

BACKGROUND OF THE INVENTION

Production of virus-like particles (VLPs) typically involves expression and assembly of the VLPs in host cell expression systems. For removing infectious agents from the resulting production cultures, virus filtration is commonly used, though other methods such as UV inactivation or chemical inactivation may also used (either alone or in conjunction with filter-based methods). However, for larger biological components such as VLPs, virus filtration is not available as the VLPs are often too close in size to infectious agents (e.g., viruses) to be capable of being separated from such infectious agents by filtration alone.

In a particular example, following baculovirus expression of VLPs in Sf9 insect cells, the resulting bulk production cultures contain high levels of process contaminants including host cell proteins, nucleic acids and live infectious agents, including baculovirus. While harvest of VLP production culture by low speed centrifugation and filtration generates a clarified sample suitable for downstream purification, these methods are not suitable for removal of host cell protein and live viruses, including baculovirus. Therefore, other methods are needed to inactivate infectious agents and/or clear process contaminants during harvest to facilitate downstream processing when preparing VLPs.

SUMMARY OF THE INVENTION

Provided herein are methods useful for clearing process contaminants from VLP cell lysates and production cultures, and the VLP compositions produced thereby. In one embodiment, the methods of the invention comprise generating or obtaining a cell lysate, culture supernatant, or filtrate containing said VLPs, and adjusting the pH of the lysate, supernatant or filtrate to a pH value less than about 5 to generate a pH-adjusted solution. The method further comprises removing non-VLP particulates/aggregates from the pH-adjusted solution to generate a purified solution comprising the VLPs.

In some embodiments, the pH treatment methods of the present invention are useful for separating structurally diverse populations of VLPs, where the VLPs comprise at least a first subpopulation and a second subpopulation of the VLPs. Separating the non-VLP particulates/aggregates may comprise separating the second subpopulation of VLPs from the pH-adjusted solution to generate the purified solution, wherein the purified solution substantially retains the first subpopulation of VLPs. The method may further comprise, after separating the second subpopulation of VLPs from the purified solution, separating the first population of VLPs from the purified solution. In some embodiments, the VLP is a norovirus VLP, wherein the first subpopulation comprises norovirus VLP with a full length VP1 subunit, and wherein the second subpopulation comprises norovirus VLP with a truncated VP1 subunit. The ratio of the first subpopulation of VLPs to residual contaminating protein is increased to at least about 50% following such treatment. In some embodiments, the ratio of the first subpopulation of VLPs to residual contaminating protein is increased to at least about 80% following such treatment.

In some embodiments, separating comprises one or more of the following processes: centrifugation, precipitation, flocculation, settling, and filtration. In some embodiments, removing the VLPs comprises separating a first subpopulation of VLPs from the purified solution using one or more chromatographic processes.

In some aspects of the invention, a method for purifying VLPs comprises generating or obtaining a cell lysate, culture supernatant, or filtrate containing VLPs, and purifying the VLPs using a multistep chromatographic process to generate a purified solution. At least one chromatographic process of the multistep chromatographic process comprises contacting the lysate, supernatant or filtrate with a chromatographic material, wherein the VLPs bind to said chromatographic material; treating the chromatographic material with a solvent and/or detergent; and eluting, after said treating, the VLPs from the chromatographic material. Each chromatographic process is independently selected from: hydroxyapatite chromatography, hydrophobic interaction chromotography, size exclusion chromatography, ion exchange chromatography, mixed mode chromatography, membrane-based chromatography, and affinity chromatography. In some embodiments, a first chromatographic process of the multistep chromatographic process is ion exchange chromatography, wherein the ion exchange chromatography is selected from anion exchange chromatography and cation exchange chromatography.

In some embodiments, a first chromatographic process of the multistep chromatographic process is cation exchange chromatography, and said treating step is performed on a cation exchange column of the cation exchange chromatography process. In some embodiments, a first chromatographic process of the multistep chromatographic process is hydroxyapatite chromatography, and said treating step is performed on a hydroxyapatite column of the hydroxyapatite chromatography process. In some embodiments, the first chromatographic process of the multistep chromatographic process is affinity chromatography, and said treating step is performed on an affinity column of the affinity chromatography process. In some embodiments, the first chromatographic process of the multistep chromatographic process is mixed mode chromatography, and said treating step is performed on a mixed mode column of the mixed mode chromatography process. In some embodiments, the first chromatographic process of the multistep chromatographic process is hydrophobic interaction chromatography, and said treating step is performed on a hydrophobic interaction column of the hydrophobic interaction chromatography process. In some embodiments, the method further comprises one or more additional chromatographic processes.

The solvent and/or detergent comprises one or more of the following: Tributyl phosphate (TnBP), nonionic detergents (including Triton X-100 and polyoxyethylene sorbitan monooleate), zwiterionic detergents (including CHAPS and Zwittergent 3-12) and ionic detergents (including sodium cholate and Dimethyldioctadecylammonium bromide).

In some embodiments, the VLPs are one or more of: norovirus genogroup I VLPs, norovirus genogroup II VLPs, norovirus genogroup IV VLPs, chimeric norovirus VLPs, engineered norovirus VLP variants, and sapovirus VLPs. In some embodiments, the VLPs are one or more sapovirus VLPs. In some embodiments, the ratio of the VLPs to residual contaminating protein is increased at least about two-fold.

In some embodiments, the ratio of the VLPs to residual contaminating protein is increased at least about ten-fold as compared to the lysate, supernatant or filtrate. In some embodiments, at least about 50% of residual contaminating protein is removed from the lysate, supernatant or filtrate. In some embodiments, no more than about 50% of the VLPs are lost during said purification.

In some embodiments, the lysate, supernatant or filtrate is generated using recombinant methodologies, and the VLPs are produced in bacterial cells, insect cells, yeast cells, or mammalian cells. The VLPs may also be produced in plant cells.

In some aspects of the invention, a method of purifying VLPs comprises generating or obtaining a cell lysate or culture supernatant/filtrate containing VLPs, said VLPs comprising at least a first subpopulation and a second subpopulation of the VLPs. The method further comprises adjusting the pH of the lysate, supernatant or filtrate to a pH of less than about 5, and removing the second subpopulation of VLPs from the pH-adjusted solution using a filtration process to generate a filtered solution. The filtered solution substantially retains the first subpopulation of VLPs. The method additionally comprises separating the first subpopulation of VLPs from the filtered solution using a multistep chromatographic process which incorporates at least one on-column solvent and/or detergent treatment step. In some embodiments, the ratio of the first population of VLPs to residual contaminating protein is increased at least about two-fold. In some embodiments, the filtration process includes a depth filtration process.

In some embodiments, the VLPs are one or more of: norovirus genogroup I VLPs and norovirus genogroup II VLPs. In other embodiments, the VLPs are one or more of norovirus genogroup IV VLPs and other norovirus genogroups which are determined to infect humans in the future.

In some aspects of the invention, a method of purifying VLPs comprises generating or obtaining a cell lysate, culture supernatant, or filtrate containing VLPs. The method further comprises adjusting the pH of the lysate, supernatant or filtrate to a pH of less than about 5 to generate a pH-adjusted solution. The method additionally comprises removing non-VLP particulates/aggregates from the pH-adjusted solution to generate a purified solution, said removing including clarifying the pH-adjusted solution by a depth filtration process to generate a purified, depth-filtered solution. In some embodiments, the depth filtration process comprises contacting the pH-adjusted solution with one or more depth filters to generate the purified solution. In some embodiments, at least one of the depth filters is a diatomaceous earth depth filter. In some embodiments, the one or more depth filters are a plurality of diatomaceous earth depth filters each having a filter capacity independently selected from a range of about 50 liters/m$^2$ to about 1000 liters/m$^2$. In some embodiments, the one or more depth filters is a single depth filter each having a filter capacity selected from a range of about 150 liters/m$^2$ to about 400 liters/m$^2$. In some embodiments, at least about 95% of residual contaminating nucleic acid is removed from the pH-adjusted solution as compared to the lysate, supernatant or filtrate. In some embodiments, at least about 75% of the VLPs are recovered from the pH-adjusted solution as compared to the lysate, supernatant or filtrate.

In some aspects of the invention, a solution of the invention comprises a purified population of norovirus VLPs, wherein said solution contains no more than 10% residual contaminating protein relative to VLP as measured by size-exclusion chromatography and ELISA. In some embodiments, the solution is purified from a cell lysate, culture supernatant, or filtrate containing the norovirus VLPs. In some embodiments, the solution contains no more than 35% residual contaminating nucleic acid relative to the lysate, supernatant or filtrate. In some embodiments, at least about 50% of the norovirus VLPs in the lysate, supernatant or filtrate are recovered. In some embodiments, the ratio of the norovirus VLPs to residual contaminating protein is increased at least about ten-fold as compared to the lysate, supernatant or filtrate.

In some aspects of the invention, a solution of the invention comprises a purified population of VLPs, wherein said solution contains at least about 50% VLPs with a full length VP1 subunit. In some embodiments, the solution contains up to about 100% VLPs with the full length VP1 subunit. In some embodiments, the solution is substantially free of VLPs with a truncated VP1 subunit. In some embodiments, the solution is generated from a starting material containing at least about 10% VLPs with a truncated VP1 subunit. In some embodiments, the starting material is a cell lysate, culture supernatant, or filtrate containing the VLPs.

In some aspects of the invention, a method of clearing and/or inactivating live virus in a solution containing the live virus and further containing VLPs generated by the live host cell virus, comprises adjusting the pH of the solution to a pH value less than about 5 to generate a pH-adjusted solution. In some embodiments, the level of live virus in the pH-adjusted solution is reduced at least about $10^4$ fold. In some embodiments, the level of live virus in the pH-adjusted solution is reduced at least about $10^5$ fold. The live virus can include, but is not limited to host cell virus, production virus (e.g. baculovirus), and other contaminating viruses, such as due to human handling.

In some embodiments, the method further comprises removing non-VLP particulates/aggregates from the pH-adjusted solution to generate a purified solution, and purifying the purified solution using at least one chromatographic process. The at least one chromatographic process comprises contacting the purified solution with a chromatographic material, wherein the VLPs bind to said chromatographic material and treating the chromatographic material with a solvent and/or detergent. The at least one chromatographic process further comprises eluting, after said treating, the VLPs from the chromatographic material to generation an eluate. In some embodiments, the level of live virus in the eluate is reduced by at least about $10^2$ compared to the solution containing the live virus.

In some aspects of the invention, a method of clearing and/or inactivating live virus in a solution containing the live virus and further containing VLPs generated by the live virus, comprises purifying the solution containing the live virus using at least one chromatographic process. The at least one chromatographic process comprises contacting the solution containing the live virus with a chromatographic material, wherein the VLPs bind to said chromatographic material, and treating the chromatographic material with a solvent and/or detergent. The at least one chromatographic process further comprises eluting, after said treating, the VLPs from the chromatographic material to generation an eluate. In some embodiments, the level of live residual contaminating virus in the eluate is reduced at least about $10^5$ compared to the solution containing the live virus. In some embodiments, the level of live virus in the eluate is reduced at least about $10^7$ compared to the solution containing the live virus.

The present invention also comprises the VLP compositions produced by the methods disclosed herein, and vaccine compositions comprising the VLPs in addition to one or more adjuvants and/or excipients. The VLP compositions produced herein are advantageous in that they have less process contaminants and are substantially free of aberrant VLP structures formed during production.

BRIEF DESCRIPTION OF THE DRAWINGS

FIG. 1A, illustrating a low pH treatment, is a stained SDS-PAGE gel of the Norwalk VP1 subunit as the prominent band, where Lane 1 is bulk Norwalk VLP production culture (total); lane 2 is VLP production culture-microfuge supernatant/filtrate; lane 3 is VLP production culture-microfuge pellet; lane 4 is bulk VLP production culture following low pH treatment (total); and lane 5 is VLP production culture following low pH treatment, low-speed centrifugation and 0.2 μm filtration (final harvest material);

FIG. 1B, illustrating the low pH treatment, is a stained SDS-PAGE gel with the Consensus VP1 subunit as the prominent band, where Lane 1 is bulk Consensus VLP production culture (total); and lane 2 is VLP production culture following low pH treatment, low-speed centrifugation and 0.2 μm filtration (final harvest material);

DETAILED DESCRIPTION OF THE INVENTION

Figures 2A, 2B:
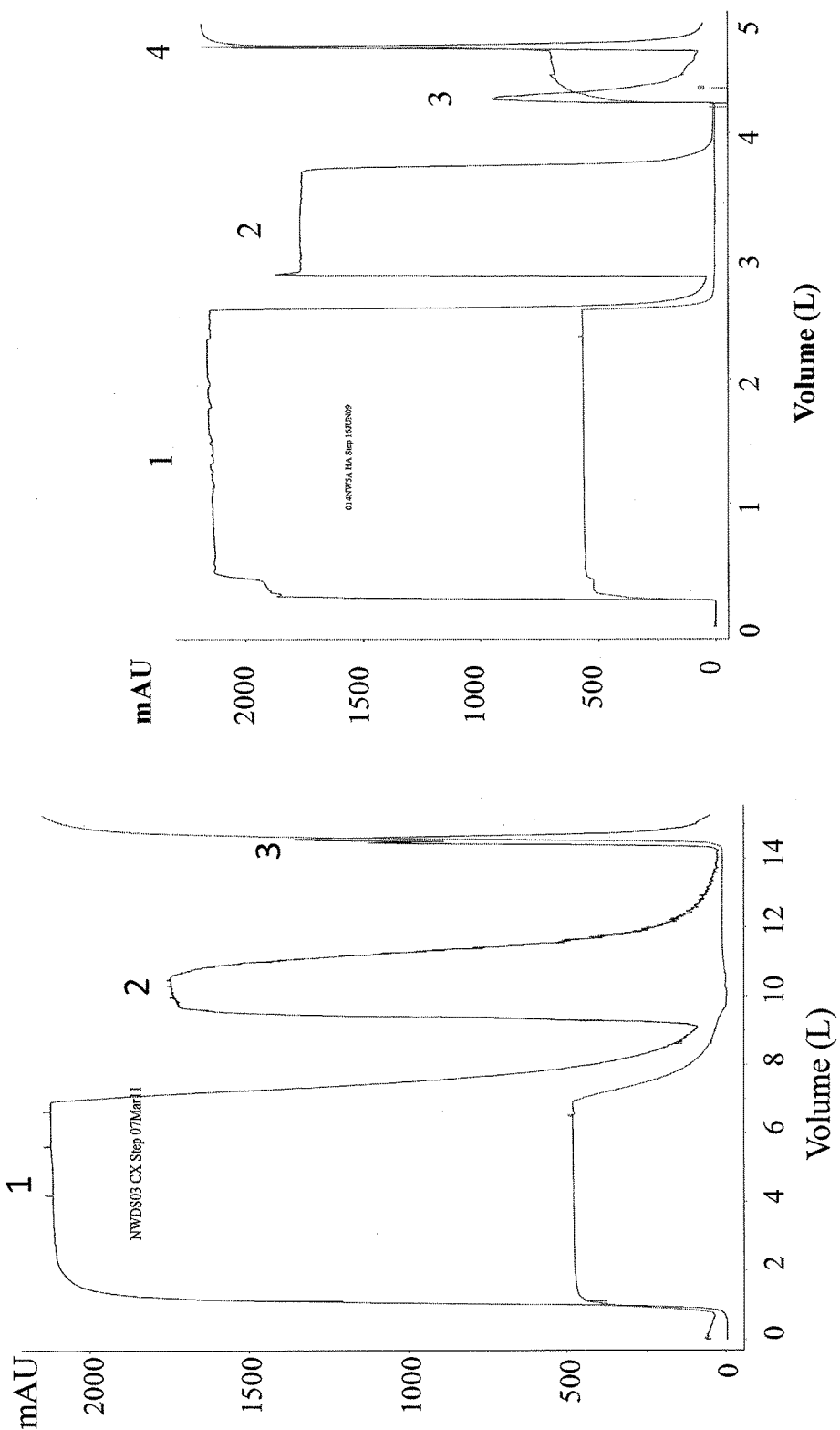
FIG. 2A, illustrating the solvent/detergent treatment, is a representative chromatogram for the bind and elute unit operations during cation-exchange capture chromatography, where Norwalk VLP Conditioned Media was loaded on a 180 mL bed volume Sartobind S capsule at 100 mL/min. The chromatogram shows: 1) loading of Conditioned Media; 2) solvent/detergent wash; and 3) elution of Norwalk VLPs.
FIG. 2B, illustrating the solvent/detergent treatment, is a representative chromatogram for the bind and elute unit operations during hydroxyapatite capture chromatography, where Norwalk VLP Conditioned Media was loaded on a 250 mL bed volume hydroxyapatite column at 80 mL/min. The chromatogram shows: 1) loading of Conditioned Media; 2) solvent/detergent wash; and 3) 100 mM phosphate wash; and 4) elution of Norwalk VLPs.

The present invention relates to preparation of solutions and/or vaccine compositions, and particularly to methods of purifying VLPs. In particular, the present inventors have found that a low pH treatment step of VLP production cultures provides for beneficial clearance of process contaminants such as live host cell virus and residual contaminating protein, as well some variants of the VLP population, while maintaining the immunogenicity and integrity of VLP structure. For example, for purification of norovirus VLPs, the present inventors have found that a low pH-treatment step results in substantial removal and/or inactivation of live viruses and norovirus VLPs having a truncated VP1 subunit.

It is understood that aspects of the present invention are applicable to purification of any VLP, and variants thereof. In some embodiments, the VLP is of a virus that belongs to the Caliciviridae family. In some embodiments, the VLPs are norovirus VLPs, including chimeric or engineered variants. In some embodiments, the VLPs are sapovirus VLPs.

It is also understood that aspects of the present invention are applicable for VLP purification that results in removal of live virus infectious agents. In some embodiments, the live virus is a non-enveloped virus such as, for example, a parvovirus, a rotavirus, and/or the like. In some embodiments, the live virus is an enveloped virus such as, for example, a baculovirus, a retrovirus, an errantivirus, an arbovirus, respiratory synctial virus, and/or the like.

Additionally, the present inventors have found that a treatment with a solvent and/or detergent is a useful step for inactivating and removing viral contaminants, including remaining baculovirus if VLPs are produced using the baculovirus expression system. Accordingly, the methods of the invention may additionally or alternatively comprise at least one chromatographic process that involves either treating a chromatographic material (e.g. of a chromatography column) which is in contact with a composition that comprises the VLPs with a solvent and/or detergent, and/or adding the solvent/detergent to the composition that comprises the VLPs prior to contact with the chromatographic material. This is followed by elution of the VLPs from the chromatographic material and applying SDR Hyper-D for removal of residual solvent/detergent.

Additionally, the present inventors have found that depth filtration with one or more depth filters, such as diatomaceous earth and/or synthetic depth filters for example, is a useful step for removing residual contaminating nucleic acid, including baculovirus nucleic acid if VLPs are produced using the baculovirus expression system. Accordingly, the methods of the invention may additionally or alternatively comprise clarifying any solution containing VLPs and residual contaminating nucleic acid by a depth filtration process to generate a purified, depth-filtered solution.

The present inventors have also found that the purified solution(s) generated by one or more of the abovementioned processes beneficially result in reduction of residual contaminating protein relative to VLP in the purified solution, as compared to any pre-purification solution. Accordingly, the solutions of the invention may show reduction in residual contaminating protein relative to VLP as a result of the purification.

The present inventors have also found that the purified solution(s) generated by one or more of the abovementioned processes beneficially result in a relative increase of VLP levels of VLPs with a full length VP1 subunit as compared to any pre-purification solution. Accordingly, the solutions of the invention may show increased levels of VLPs with a full length VP1 subunit as a result of the purification.

A method for purifying virus like particles (VLPs) comprises generating or obtaining acell lysate, culture supernatant, or filtrate containing said VLPs. The method also comprises adjusting the pH of the lysate, supernatant or filtrate to a pH value less than about 5 to generate a pH-adjusted solution. The method also comprises removing non-VLP particulates/aggregates from the pH-adjusted solution containing the VLPs to generate a purified solution.

In some embodiments, production of VLPs generates a cell lysate, culture supernatant, or filtrate comprising at least a first subpopulation and a second subpopulation of the VLPs as well as other process contaminant materials. In some embodiments, the lysate, supernatant or filtrate is a bulk production culture, or is generated from a bulk production culture. In some embodiments, the lysate, supernatant or filtrate is obtained from a culture supernatant that has been pre-cleared by filtration and/or centrifugation.

In some embodiments, the subpopulations of the VLPs are characterized based on their differential response to pH treatment, based on the antigenic response elicited, and/or based on structural differences. Accordingly, it is envisioned that more than two subpopulations of the VLPs may exist, depending on the virus. In some embodiments, the generated VLP is a norovirus VLP, the first subpopulation comprises norovirus VLP with a full length VP1 subunit, and the second subpopulation comprises norovirus VLP with a truncated VP1 subunit. In some embodiments, the norovirus VLPs are one or more of norovirus genogroup I VLPs, norovirus genogroup II VLPs, norovirus genogroup III VLPs, norovirus genogroup IV VLPs, and norovirus genogroup V VLPs. In some embodiments, the VLPs are acid-stable VLPs.

The methods of the invention include adjusting the pH of the lysate, supernatant or filtrate to separate the VLPs from process contaminants and aberrantly formed VLP-like structures. Process contaminants may include, but are not limited to, polysaccharides, residual contaminating proteins such as host cell proteins, residual contaminating nucleic acid such as host cell nucleic acid, lipids, media components, live infectious agents such as live host cell viruses (e.g. baculoviruses), and the like, as well as assemblies or aggregates of any of the foregoing contaminants. An aberrantly formed VLP-like structure may be any VLP structure that is distinguishable from a desirable VLP structure based on their differential response to environmental conditions (for example, pH treatment or temperature), the antigenic response elicited, structural differences, separation profiles (for example, chromatographic, sedimentation, or filtration), and/or the like.

In some embodiments, the pH of the lysate, supernatant or filtrate is adjusted to less than about 5 to generate the pH-adjusted solution. In some embodiments, the pH of the lysate, supernatant or filtrate is adjusted to less than about 4.5, to less than about 4, to less than about 3.5, to less than about 3.4, to less than about 3.3, to less than about 3.2, to less than about 3.1, to less than about 3, to less than about 2.9, to less than about 2.8, to less than about 2.7, to less than about 2.6, to less than about 2.5, to less than about 2, to less than about 1.5, to less than about 1, and all ranges/subranges in between.

The pH of the lysate, supernatant or filtrate may be adjusted by any method known to one of skill in the art. In some embodiments, the pH is adjusted by addition of one or more reagents to the lysate, supernatant or filtrate that result in acidification. Exemplary acidification reagents may include: hydrochloric acid, acetic acid, sulfuric acid, and phosphoric acid. The pH, volume, and composition of the added reagents(s) may be suitably selected as is known in the art.

In some embodiments, the duration of pH adjustment and/or treatment of the lysate, supernatant or filtrate is about 30 minutes. In some embodiments, the duration of pH adjustment and/or treatment of the lysate, supernatant or filtrate is about 1 hour, is about 2 hours, is about 3 hours, is about 4 hours, is about 5 hours, is about 10 hours, is about 15 hours, is about 20 hours, is about 25 hours, is about 30 hours, is about 35 hours, is about 40 hours, is about 45 hours, is about 46 hours, is about 47 hours, is about 48 hours, and all ranges/subranges in between.

In some embodiments, the lysate, supernatant or filtrate comprises a first subpopulation and a second subpopulation of VLPs as discussed earlier, and adjusting the pH of the lysate, supernatant or filtrate results in a heterogeneous distribution of the first and second subpopulations. In some embodiments, the pH treatment results in particulate and/or aggregate formation in the pH-adjusted solution, the second subpopulation of VLPs is substantially found in the resulting particulates/aggregates, and the first subpopulation of VLPs remain in the volume of the pH-adjusted solution. In some embodiments, as exemplified with the norovirus genogroup II VLPs purified herein, the second subpopulation comprises VLPs containing truncated VP1 proteins, in contrast to the first subpopulation which comprises VLPs with full length VP1 proteins.

In some embodiments, the method of purifying VLPs further includes removing the non-VLP particulates/aggregates from the pH-adjusted solution to generate the purified solution. In some embodiments, removing includes, but is not limited to, one or more of the following processes: centrifugation, precipitation, flocculation, settling, and filtration. In some embodiments, separation involves at least centrifugation to remove the particulates/aggregates.

In some embodiments, removing the non-VLP particulates/aggregates includes separating the second subpopulation of VLPs from the pH-adjusted solution to generate the purified solution, wherein the purified solution substantially retains the first subpopulation of VLPs. In other words, the particulates/aggregates comprise the second subpopulation of VLPs. In this manner, selective removal of an undesirable subpopulation of VLPs may be achieved at an early stage of the harvest process, i.e., during culture clarification.

In some embodiments, the removal/clarification is done by one or more filtration processes. Suitable filtration include, but are not limited to, depth-filtration, membrane filtration, chemical filtration, and/or the like. In some embodiments, at least one filtration process is depth filtration using one or more depth filters. Depth filtration can refer to any filtration process that employs a porous filter/filtration medium. Suitable depth filters include, but are not limited to, diatomaceous earth depth filters, synthetic depth filters, and/or the like. Benefits of using depth filtration include ease of operation and availability of disposable materials that eliminate the requirement for cleaning validation required for reused equipment. In some embodiments, one or more additional filtration processes, such as using a sub-micron filter, can be optionally employed as well.

In some embodiments, the ratio of the first subpopulation of VLPs to residual contaminating protein is increased at least about two-fold after this step. In some embodiments, the ratio of the first subpopulation of VLPs to residual contaminating protein is increased at least about three-fold, at least about four-fold, at least about five-fold, at least about ten-fold, at least about fifteen-fold, at least about twenty-fold, at least about fifty-fold, at least about seventy-five-fold, at least about one-hundred-fold, and all values in between.

In some embodiments, at least about 50% of residual contaminating nucleic acid is removed from the lysate, supernatant or filtrate after filtration. The term 'residual contaminating nucleic acid' can include, but is not limited to, host cell nucleic acid, nucleic acid of host cell viruses, nucleic acid of the production virus (i.e. used to produce the VLPs), and/or the like. In some embodiments, at least about 55% of residual contaminating nucleic acid, at least about 60%, at least about 61%, at least about 62%, at least about 63%, at least about 64%, at least about 65%, at least about 66%, at least about 67%, at least about 68%, at least about 69%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, and all values in between, is removed from the lysate, supernatant or filtrate.

In general, the extent of purification of the VLPs after the specified processing step may be measured (against the lysate, supernatant or filtrate) by the change in a ratio of the concentration of the VLPs to the concentration of any other component. For example, the ratio may be calculated between VLP concentration and infectious agent concentration, between VLP concentration and residual contaminating protein, and/or between VLP concentration and host cell process contaminants.

In some embodiments, purifying the VLPs also encompasses, after removing the second subpopulation of VLPs from the pH-adjusted solution, separating the first population of VLPs from the purified solution. In some embodiments, separating the first population of VLPs from the purified solution includes any suitable separation process(es) such as, for example, centrifugation (e.g. continuous flow), precipitation, phase-separation, tangential flow filtration, buffer exchange methods, and/or the like. In some embodiments, separating the first population of VLPs from the purified solution includes using one or more chromatographic processes. Each chromatographic process may be independently selected from, but is not limited to, hydroxyapatite chromatography, hydrophobic interaction chromtography, size exclusion chromatography, ion exchange chromatography, mixed mode chromatography and affinity chromatography. Ion exchange chromatography can be anion exchange chromatography or cation exchange chromatography.

In some embodiments, the ratio of the first subpopulation of VLPs to residual contaminating protein is increased at least about two-fold after this step. In some embodiments, the ratio of the first subpopulation of VLPs to residual contaminating protein is increased at least about three-fold, at least about four-fold, at least about five-fold, at least about ten-fold, at least about fifteen-fold, at least about twenty-fold, at least about fifty-fold, at least about seventy-five-fold, at least about one-hundred-fold, and all values in between. In some embodiments, at least about 50% of residual contaminating nucleic acid is removed from the lysate, supernatant or filtrate after this step. The term 'residual contaminating nucleic acid' can include, but is not limited to, host cell nucleic acid, production virus nucleic acid, viral nucleic acid, bacterial nucleic acids, fungal nucleic acids, nucleic acids from other organisms that may or may not be related to the systems and methods described herein, and/or the like. In some embodiments, at least about 55% of residual contaminating nucleic acid, at least about 60%, at least about 61%, at least about 62%, at least about 63%, at least about 64%, at least about 65%, at least about 66%, at least about 67%, at least about 68%, at least about 69%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, and all values in between, is removed from the lysate, supernatant or filtrate.

The present inventors have also found that a solvent and/or detergent treatment step is useful for purifying live virus infectious agent (e.g. baculovirus) away from VLP preparations. As noted earlier, the solvent and/or detergent can be added to the VLP preparation either prior to contact with a chromatography column, and/or can be added to the bulk solutions prior to contact with the chromatography column, and/or can be can be added to the chromatography column after contact with the VLP preparation. Hence, although described herein with respect to on-column solvent/detergent treatment for simplicity, it is understood that each of these possibilities is within the scope of the invention. In such embodiments, the inventive methods comprise generating or obtaining a cell lysate, culture supernatant, or filtrate containing VLPs, and purifying the VLPs using a multistep chromatographic process. At least one chromatographic process of the multistep chromatographic process comprises contacting the lysate, supernatant or filtrate with a chromatographic material, wherein the VLPs bind to said chromatographic material. The at least one chromatographic process also comprises treating the chromatographic material with a solvent and/or detergent. The at least one chromatographic process further comprises eluting, after treating, the VLPs from the chromatographic material.

In some embodiments, the at least one chromatographic process also includes treating the chromatographic material with a solvent and/or detergent. In some embodiments, the chromatographic material is a chromatography column, and treating encompasses on-column treatment or washing with the solvent and/or detergent. Any suitable solvent and/or detergent may be employed. In some embodiments, the solvent is an organic solvent and includes, but is not limited to, one or more of the following: Tributyl phosphate (TnBP). In some embodiments, the detergent includes, but is not limited to, one or more of the following: Triton X-100, octylphenol ethyleneoxide condensate, polyoxyethylene sorbitan monooleate, and sodium cholate, and various combinations thereof. Exemplary compositions are: nonionic detergents (including Triton X-100 and polyoxyethylene sorbitan monooleate), zwiterionic detergents (including CHAPS and Zwittergent 3-12) and ionic detergents (including sodium cholate and Dimethyldioctadecylammonium bromide).

In some embodiments, the solvent and/or detergent comprises at least about 0.01% detergent (w/v), at least about 0.1%, at least about 0.2%, at least about 0.3%, at least about 0.4%, at least about 0.5%, at least about 1%, at least about 2%, at least about 3%, at least about 4%, at least about 5%, at least about 10% detergent (w/v), and all values in between. In some embodiments, the solvent and/or detergent comprises at least about 0.01% solvent (w/v), at least about 0.1%, at least about 0.2%, at least about 0.3%, at least about 0.4%, at least about 0.5%, at least about 1%, at least about 2%, at least about 3%, at least about 4%, at least about 5%, at least about 10% solvent (w/v), and all values in between. In some embodiments, the solvent and/or detergent additionally contains commonly-used biological buffer(s) (e.g. acetate, citrate, histidine, phosphate, Tris, and/or the like) and/or salt(s) (e.g. sodium chloride, potassium chloride, magnesium chloride, and/or the like).

In some embodiments, the duration of treatment with the solvent and/or detergent is about 10 minutes. In some embodiments, the duration of treatment with the solvent and/or detergent is about 20 minutes, is about 30 minutes, is about 1 hour, is about 2 hours, is about 3 hours, is about 4 hours, is about 5 hours, is about 10 hours, is about 15 hours, is about 20 hours, is about 21 hours, is about 22 hours, is about 23 hours, is about 24 hours, and all ranges/subranges in between.

In some embodiments, the cell lysate or the culture supernatant/filtrate is generated using recombinant methodologies, as discussed earlier. In some embodiments, the VLPs are produced in one or more of the following: bacterial cells, insect cells, yeast cells, plant or mammalian cells. In some embodiments, the VLPs are norovirus genogroup I VLPs, norovirus genogroup II VLPs and/or norovirus genogroup IV VLPs.

In some embodiments, purifying the VLPs includes purifying the VLPs using a multistep chromatographic process. Each chromatographic process is independently selected as listed earlier. In some embodiments, a first chromatographic process of the multistep chromatographic process is cation exchange chromatography, and one or more subsequent chromatographic processes may be employed as well.

In some embodiments, at least one chromatographic process involves contacting the lysate, supernatant or filtrate with a chromatographic material, wherein the VLPs bind to said chromatographic material. The chromatographic material used depends on the particular chromatographic process being employed and may include, but is not limited to, a cation exchange column, a hydroxyapatite column, a hydrophobic interaction column, a size exclusion column, an anion exchange column, a mixed mode column, or an affinity column, and the like. When the at least one chromatographic process is cation exchange chromatography, the chromatographic material is a cation exchange column or membrane.

In some embodiments, the at least one chromatographic process also includes eluting, after on-column treatment, the VLPs from the chromatographic material. The elution mechanism may depend on experimental factors such as, but not limited to, choice of the chromatographic process, the solvent and/or detergent used, the interaction between the VLPs/chromatographic matrix and the eluent, and so on. The elution may be carried out by adjusting the pH and/or ionic strength of the chromatography system with any suitable and commonly-used biological buffer(s) (acetate, citrate, histidine, phosphate, Tris) and salt(s) (sodium chloride, potassium chloride, magnesium chloride) as known in the art. In some embodiments, the at least one chromatographic process is cation exchange chromatography, and the elution is carried out by washing the cation exchange column with acetate. In another embodiment, the at least one chromatographic process is hydroxyapatite chromatography, and the elution is carried out by washing the hydroxyapatite column with sodium phosphate.

In some embodiments, the ratio of the VLPs to residual contaminating protein is increased about two-fold as compared to the lysate, supernatant or filtrate after the at least one chromatographic process involving solvent and/or detergent treatment. The term 'residual contaminating protein' can include, but is not limited to, host cell protein, protein components from the host cell virus, production virus nucleic acid, viral nucleic acid, bacterial nucleic acids, fungal nucleic acids, nucleic acids from other organisms that may or may not be related to the production systems, and/or the like. In some embodiments, the ratio of the VLPs to residual contaminating protein is increased at least three-fold, at least four-fold, at least five-fold, at least ten-fold, at least fifteen-fold, at least twenty-fold, at least fifty-fold, at least seventy-five-fold, at least eighty-fold, at least eighty five-fold, at least ninety-fold, at least ninety-five fold, at least one-hundred-fold, and all values in between. In some embodiments, the ratio of the VLPs to residual contaminating protein is increased about two-fold after the multistep chromatographic process. In some embodiments, the ratio of the VLPs to residual contaminating protein is increased about three-fold, about four-fold, at least about five-fold, at least about ten-fold, at least about fifteen-fold, at least about twenty-fold, at least about fifty-fold, at least about seventy-five-fold, at least about eighty-fold, at least about eighty five-fold, at least about ninety-fold, at least about ninety-five fold, at least about one-hundred-fold, and all values in between.

In some embodiments, at least about 30% of residual contaminating protein is removed from the lysate, supernatant or filtrate after the at least one chromatographic process involving solvent and/or detergent treatment. In some embodiments, at least about 35%, at least about 40%, at least about 45%, at least about 46%, at least about 47%, at least about 48%, at least about 49%, at least about 50%, at least about 51%, at least about 52%, at least about 53%, at least about 54%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, and all values in between, of residual contaminating protein is removed from the lysate, supernatant or filtrate.

In some embodiments, none of the VLPs in the lysate, supernatant or filtrate are lost after the at least one chromatographic process involving solvent and/or detergent treatment. In some embodiments, no more than about 1%, no more than about 2%, no more than about 3%, no more than about 4%, no more than about 5%, no more than about 6%, no more than about 7%, no more than about 8%, no more than about 9%, no more than about 10%, no more than about 15%, no more than about 20%, no more than about 25%, no more than about 30%, no more than about 35%, no more than about 40%, no more than about 45%, no more than about 50%, no more than about 50%, no more than about 55%, no more than about 60%, and all values in between, of the VLPs in the lysate, supernatant or filtrate are lost after the at least one chromatographic process involving solvent and/or detergent treatment.

In some embodiments, about 100% of the VLPs are recovered from the lysate, supernatant or filtrate after the at least one chromatographic process involving solvent and/or detergent treatment. In some embodiments, at least about 99%, at least about 98%, at least about 97%, at least about 96%, at least about 95%, at least about 94%, at least about 93%, at least about 92%, at least about 91%, at least about 90%, at least about 85%, at least about 80%, at least about 75%, at least about 70%, at least about 65%, at least about 60%, at least about 55%, at least about 50%, at least about 45%, at least about 40%, and all values in between, of the VLPs are recovered from the lysate, supernatant or filtrate after the at least one chromatographic process involving solvent and/or detergent treatment.

In some embodiments, the inventive methods described herein also provide for clearing and/or inactivating live virus in a solution containing the live virus and further containing VLPs generated by the live virus, where the method includes adjusting the pH of the solution containing the live virus to a pH value less than about 5 to generate a pH-adjusted solution. The live virus can be, but is not limited to, live host cell virus, production virus (baculovirus, for example), contaminating virus that may or may not be related to the production systems, and/or the like. The VLPs can be, but are not limited to, genogroup I VLPs and/or genogroup II VLPs.

In some embodiments, the level of live virus in the pH-adjusted solution is at least about 10-fold lower than the solution containing the live virus. In some embodiments, the level of live virus in the pH-adjusted solution is at least about 100-fold, at least about $10^3$-fold, at least about $10^4$-fold, at least about $10^5$-fold, at least about $10^6$-fold, at least about $10^7$-fold, at least about $10^8$-fold, at least about $10^9$-fold, at least about $10^{10}$-fold, and all values in between, lower than the solution containing the live virus.

In some embodiments, non-VLP particulates/aggregates can be removed from the pH-adjusted solution to generate a purified solution, which can then be treated by at least one chromatographic process. The at least one chromatographic process can include contacting the purified solution with a chromatographic material, where the VLPs bind to the chromatographic material, and treating the chromatographic material with a solvent and/or detergent. The at least one chromatographic process can also include eluting, after treating, the VLPs from the chromatographic material to generate an eluate. In some embodiments, the level of live virus in the eluate is reduced by at least about $10^2$-fold compared to the solution containing the live virus. In some embodiments, the level of live virus in the eluate is reduced by at least about $10^3$-fold, at least about $10^4$-fold, at least about $10^5$-fold, at least about $10^6$-fold; at least about $10^7$-fold, at least about $10^8$-fold, at least about $10^9$-fold, at least about $10^{10}$-fold, at least about $10^{11}$-fold, at least about $10^{12}$-fold, at least about $10^{13}$-fold, at least about $10^{14}$-fold, at least about $10^{15}$-fold, at least about $10^{16}$-fold, and all values in between, compared to the solution containing the live virus.

In some embodiments, the inventive methods described herein also provide for clearing and/or inactivating live virus in a solution containing the live virus and further containing VLPs generated by the live virus, where the method includes purifying the solution containing the live virus using at least one chromatographic process. The at least one chromatographic process can include contacting the solution with a chromatographic material, where the VLPs bind to the chromatographic material, and treating the chromatographic material with a solvent and/or detergent. The at least one chromatographic process can also include eluting, after treating, the VLPs from the chromatographic material to generate an eluate. In some embodiments, the level of live virus in the eluate is reduced by at least about 10-fold compared to the solution containing the live virus. In some embodiments, the level of live virus in the eluate is reduced by at least about $10^2$-fold, at least about $10^3$-fold, at least about $10^4$-fold, at least about $10^5$-fold, at least about $10^6$-fold, at least about $10^7$-fold, at least about $10^8$-fold, at least about $10^9$-fold, at least about $10^{10}$-fold, and all values in between, compared to the solution containing the live virus.

In some embodiments, the invention is further operable for purifying virus like particles (VLPs) from a lysate, supernatant or filtrate containing the VLPs using a low pH treatment step and a filtration process/step to remove process contaminant and/or a secondary subpopulation of VLPs, as well as at least one chromatographic process involving on-column solvent and/or detergent treatment to inactivate live virus infectious agent. In some embodiments, the first subpopulation includes norovirus VLPs with full length VP1 subunit, and the second subpopulation includes norovirus VLPs with truncated VP1 subunit. The lysate, supernatant or filtrate is generated by any suitable means, as described earlier.

Adjusting the pH of the lysate, supernatant or filtrate is carried out in a manner similar to already described, including conditions of pH value (e.g. less than about 5), duration of treatment (e.g. about 30 minutes) and so on. The pH treatment results in particulate and/or aggregate formation which contains the second subpopulation of VLPs, while the first subpopulation of VLPs remain in the volume of the pH-adjusted solution.

The filtration process is carried out in a manner similar to already described, and can be a depth filtration process. The filtration step results in removal of the particulates/aggregates containing the second subpopulation of VLPs as well as process contaminants such as the residual contaminating nucleic acid, to generate a filtered, purified solution, where the first subpopulation of VLPs remain in the volume of the filtered, purified solution.

In this embodiment, the pH treatment and filtration steps are performed before the multistep chromatographic process, and purifying the VLPs includes separating the first subpopulation of VLPs from the filtered, purified solution using a multistep chromatographic process, where each chromatographic process of the multistep chromatographic process is independently selected as described earlier. The first subpopulation of VLPs binds to the chromatography material/column, which is treated with a solvent and/or detergent. Any suitable solvent and/or detergent may be employed, as listed earlier. The first subpopulation of VLPs is then eluted from the chromatographic material.

In some embodiments, the ratio of the VLPs to residual contaminating protein is increased about two-fold after the low pH treatment and the at least one chromatographic process. In some embodiments, the ratio of the VLPs to residual contaminating protein is increased about three-fold, about four-fold, at least five-fold, at least ten-fold, at least fifteen-fold, at least twenty-fold, at least fifty-fold, at least seventy-five-fold, at least one-hundred-fold, and all values in between. In some embodiments, the ratio of the VLPs to residual contaminating protein is increased about two-fold after the low pH treatment and the multistep chromatographic process. In some embodiments, the ratio of the VLPs to residual contaminating protein is increased about three-fold, about four-fold, at least five-fold, at least ten-fold, at least fifteen-fold, at least twenty-fold, and all values in between.

In some embodiments, the invention is further operable for purifying VLPs using a low pH treatment step and a depth filtration process/step to remove process contaminants and/or a undesirable subpopulations of VLPs, such as the second subpopulation of VLPs. The pH treatment step can be performed as described earlier.

The depth filtration process can include contacting the pH-adjusted solution with one or more depth filters to generate the filtered, purified solution. The one or more depth filters can be suitably selected for the purification system based on any production factors such as processing volume, particulate load or burden, product recovery, final turbidity, filter capacity, and/or the like. In some embodiments, at least one of the depth filters is a diatomaceous earth depth filter. In some embodiments, several of the depth filters are diatomaceous earth depth filters each having a filter capacity independently selected from about 50 liters/$m^2$, about 100 liters/$m^2$, about 200 liters/$m^2$, about 300 liters/$m^2$, about 400 liters/$m^2$, about 500 liters/$m^2$, about 600 liters/$m^2$, about 700 liters/$m^2$, about 800 liters/$m^2$, about 900 liters/m², to about 1000 liters/m², and all values in between. In some embodiments, a single depth filter is used having a filter capacity selected from about 150 liters/m², about 200 liters/m², about 250 liters/m², about 300 liters/m², about 350 liters/m², about 400 liters/m², and all values in between. An exemplary depth filter that can be used is the Millistak+HC pod filter.

In some embodiments, at least about 50% of residual contaminating nucleic acid is removed by the depth filtration process from the pH-adjusted solution as compared to the cell lysate or the culture supernatant/filtrate. In some embodiments, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, and all values in between, of residual contaminating nucleic acid is removed by the depth filtration process from the pH-adjusted solution as compared to the cell lysate or the culture supernatant/filtrate.

In some embodiments, about 100% of the VLPs are recovered by the depth filtration process from the pH-adjusted solution as compared to the cell lysate or the culture supernatant/filtrate. In some embodiments, at least about 99%, at least about 98%, at least about 97%, at least about 96%, at least about 95%, at least about 94%, at least about 93%, at least about 92%, at least about 91%, at least about 90%, at least about 85%, at least about 80%, at least about 75%, at least about 70%, at least about 65%, at least about 60%, at least about 55%, at least about 50%, at least about 45%, at least about 40%, and all values in between, of the VLPs are recovered by the depth filtration process from the pH-adjusted solution as compared to the cell lysate or the culture supernatant/filtrate.

In some embodiments, the recovered VLPs are the first population of VLPs. In some embodiments one or more chromatographic processes can be used to separate the first subpopulation of VLPs from the depth-filtered, purified solution, as described earlier.

In some embodiments, aspects of the invention are further operable for providing solutions of a purified population of norovirus VLPs that contains no more than 80% residual contaminating protein relative to VLP as measured by size-exclusion chromatography and ELISA. The solution of the purified population of norovirus VLPs can be generated from a cell lysate, culture supernatant, or filtrate described earlier, or from any other solution described previously, such as a pH-adjusted solution, a depth-filtered solution, and so on. In some embodiments, the solution of the purified population of norovirus VLPs is obtained by purification of a solution of a lysate, supernatant, or filtrate containing the norovirus VLPs. In some embodiments, the solution of the purified population of norovirus VLPs is generated by one or more of the following processes: pH treatment, centrifugation, precipitation, flocculation, settling, filtration, and chromatography. In some embodiments, the solution of the purified population of norovirus VLPs is generated from any processed/unprocessed solution, such as by pH treatment and filtration steps followed by a multistep chromatographic process, as described earlier.

In some embodiments, the solution of the purified population of norovirus VLPs contains no residual contaminating nucleic acid relative to the solution of cell lysate or culture supernatant/filtrate. In some embodiments, the solution of the purified population of norovirus VLPs contains no more than about 1%, no more than about 2%, no more than about 3%, no more than about 4%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, and all values in between, residual contaminating nucleic acid relative to the solution of cell lysate or culture supernatant/filtrate.

In some embodiments, the solution contains about 100% of the norovirus VLPs from the original lysate, supernatant, or filtrate. In some embodiments, the solution contains about 95%, about 90%, about 85%, about 80%, about 75%, about 70%, about 65%, about 60%, about 55%, about 50%, about 45%, about 40%, and all values in between, of the norovirus VLPs from the original lysate, supernatant, or filtrate.

In some embodiments, the ratio of the norovirus VLPs to residual contaminating protein is increased at least about fifty-fold as compared to the original lysate, supernatant, or filtrate. In some embodiments, the ratio of the norovirus VLPs to residual contaminating protein is increased at least about forty five-fold, at least about forty-fold at least about thirty five-fold, at least about thirty-fold, at least about twenty five-fold, at least about fifteen-fold, at least about ten-fold, at least about five-fold, at least about four-fold, at least about three-fold, at least about two-fold, and all values in between, as compared to the original lysate, supernatant, or filtrate.

In some embodiments, the solution of the purified population of norovirus VLPs can be employed for commercial processes, such as for clinical and large-scale manufacturing of vaccines. In some embodiments, the process volumes associated with the clinical and large-scale manufacturing processes can be as low as 20 liters. For example, in some embodiments, a vaccine can be prepared from the solution that includes the norovirus VLPs.

In some embodiments, aspects of the invention are further operable for providing solutions having a purified population of VLPs, where said solution contains at least about 50% VLPs with a full length VP1 subunit. In some embodiments, the solution having the purified population of VLPs contains at least about 55%, at least about 60%, at least about 65%, at least about 70%, at least about 75%, at least about 80%, at least about 85%, at least about 90%, at least about 95%, at least about 100%, and all values in between, VLPs with a full length VP1 subunit. Said another way, the solution having the purified population of VLPs can be substantially free of VLPs with a truncated VP1 subunit. In some embodiments, the solution having the purified population of VLPs contains at most about 5%, at most about 10%, at most about 15%, at most about 20%, at most about 25%, at most about 30%, at most about 35%, at most about 40%, at most about 45%, at most about 50%, and all values in between, VLPs with a truncated VP1 subunit.

In some embodiments, the solutions having the purified population of VLPs can be generated from an unpurified solution containing at least about 5% VLPs with a truncated VP1 subunit. In some embodiments, the unpurified solution can contain at least about 6%, at least about 7%, at least 8%, at least about 9%, at least about 10%, at least about 15%, at least about 20%, at least about 25%, at least about 30%, at least about 35%, at least about 40%, at least about 45%, at least about 50%, and all values in between, VLPs with a truncated VP1 subunit.

The unpurified solution can be any processed/unprocessed solution, including a solution of cell lysate, a culture supernatant, a filtrate, a pH-adjusted solution, and/or the like. In some embodiments, the solution having the purified population of VLPs is generated from the unpurified solution by a pH treatment step and removal of the truncated VP1 subunit from the pH treatment, as described earlier. The removing can be performed by one or more of centrifugation, precipitation, flocculation, settling, filtration, and/or the like. In some embodiments, a purified population of VLPs with a full length VP1 subunit can be generated by applying one or more chromatographic processes to the solution having the purified population of VLPs.

Advantageously, the purified VLPs produced by any of these embodiments are substantially free of live virus infectious agent. Free of infectious agents may refer to the absence of active agents that are capable of infection, such as the live host cell virus itself. In other words, the purified VLPs may contain agents that are inactive and are not capable of infection. By way of example, a sample containing baculovirus that has been treated such that the baculovirus is no longer capable of infection is free of infectious agent even though the sample still contains inactivated baculovirus. Furthermore, a sample need not be absolutely free of active agent capable of infection, but rather, the sample need only be sufficiently free of active agent so that the sample may be used for its intended purpose as a human or animal vaccine, as applicable (i.e., it meets any United States federal regulations governing the acceptable levels of infectious agent within a human or animal vaccine, as applicable).

The methods of the present invention are particularly useful as methods for scaling up VLP production for clinical and commercial manufacturing. Purification methods incorporating a low pH treatment and/or an on-column solvent and/or detergent treatment step result in at least about 50-250 mg purified VLP/L of starting culture, at least about 200-400 mg purified VLP/L, at least about 350-500 mg purified VLP/L, at least about 400-750 mg purified VLP/L, at least about 700-850 mg purified VLP/L, at least about 800-1000 mg purified VLP/L, and all ranges and subranges in between. The VLPs produced are substantially free of process contaminants and aberrant VLP structures. In this instance, substantially free means that, as can be appreciated by one of skill in the art, while it may be intended to remove all process contaminants and aberrant VLP structures, practical aspects associated with procedures described herein may not result in complete elimination of contaminants and aberrant VLP structures from the final composition, yet may be used for its intended purpose.

Embodiments of the invention are further operable to encompass a vaccine that comprises the first subpopulation of VLPs purified by the abovementioned method. Typically, such vaccines are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, glycerol, ethanol, or the like, and combinations thereof.

In addition, if desired, the vaccine may contain auxiliary substances such as wetting or emulsifying agents, pH buffering agents, or adjuvants which enhance the effectiveness of the vaccines. In some embodiments, the vaccine composition comprises one or more adjuvants in combination with the purified VLPs. Most adjuvants contain a substance designed to protect the antigen from rapid catabolism, such as aluminum hydroxide or mineral oil, and a stimulator of immune responses, such as Bordatella pertussis or Mycobacterium tuberculosis derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes; biodegradable microspheres; and Quil A.

Suitable adjuvants also include, but are not limited to, toll-like receptor (TLR) agonists, particularly toll-like receptor type 4 (TLR-4) agonists (e.g., monophosphoryl lipid A (MPL), synthetic lipid A, lipid A mimetics or analogs), aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, oil-in-water emulsions, MF59, and squalene. In some embodiments, the adjuvants are not bacterially-derived exotoxins. Preferred adjuvants include adjuvants which stimulate a Th1 type response such as 3DMPL or QS21.

Monophosphoryl Lipid A (MPL), a non-toxic derivative of lipid A from Salmonella, is a potent TLR-4 agonist that has been developed as a vaccine adjuvant (Evans et al. 2003). In pre-clinical murine studies intranasal MPL has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; Baldridge et al. 2004). MPL stimulates the induction of innate immunity through the TLR-4 receptor and is thus capable of eliciting nonspecific immune responses against a wide range of infectious pathogens, including both gram negative and gram positive bacteria, viruses, and parasites (Baldridge et al. 2004; Persing et al. 2002). Inclusion of MPL in vaccine formulations should provide rapid induction of innate responses, eliciting nonspecific immune responses from viral challenge while enhancing the specific responses generated by the antigenic components of the vaccine.

In some embodiments, the present invention provides a vaccine comprising monophosphoryl lipid A (MPL) or 3 De-O-acylated monophosphoryl lipid A (3D-MPL) as an enhancer of adaptive and innate immunity. Chemically 3D-MPL is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA), which is incorporated herein by reference. In another embodiment, the present invention provides a vaccine composition comprising synthetic lipid A, lipid A mimetics or analogs, such as BioMira's PET Lipid A, or synthetic derivatives designed to function like TLR-4 agonists.

In certain embodiments, the vaccine composition comprises two adjuvants. A combination of adjuvants may be selected from those described above. In one particular embodiment, the two adjuvants are MPL and aluminum hydroxide (e.g., alum). In another particular embodiment, the two adjuvants are MPL and oil.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation. Suitably effective increases in immunoglobulin levels include by more than 5%, preferably by more than 25%, and in particular by more than 50%, as compared to the same antigen composition without any adjuvant.

In one embodiment, the present invention provides a vaccine composition formulated for parenteral administration, wherein the composition includes purified VLPs in combination with aluminum hydroxide and a buffer. The buffer can be selected from the group consisting of L-histidine, imidazole, succinic acid, tris, citric acid, bis-tris, pipes, mes, hepes, glycine amide, and tricine. In one embodiment, the buffer is L-histidine or imidazole. Preferably, the buffer is present in a concentration from about 15 mM to about 50 mM, more preferably from about 18 mM to about 40 mM, or most preferably about 20 mM to about 25 mM. In some embodiments, the pH of the antigenic or vaccine composition is from about 6.0 to about 7.0, or from about 6.2 to about 6.8, or about 6.5. The vaccine composition can be an aqueous formulation.

In some embodiments, the vaccine composition further comprises at least one adjuvant in addition to the VLPs, aluminum hydroxide, and a buffer. For instance, the adjuvant can be a toll-like receptor agonist, such as MPL, flagellin, CpG oligos, synthetic lipid A or lipid A mimetics or analogs. In some embodiments, the adjuvant is MPL.

In one embodiment, a vaccine of the present invention may be formulated as a dry powder containing one or more purified VLP antigen(s) as the immunogen, an adjuvant such as MPL, a biopolymer such as chitosan to promote adhesion to mucosal surfaces, and bulking agents such as mannitol and sucrose. Using norovirus as a non-limiting example of a non-enveloped virus, a norovirus vaccine may be formulated as 10 mg of a dry powder containing one or more norovirus genogroup antigen(s) (e.g., Norwalk virus, Houston virus, Snow Mountain virus), MPL adjuvant, chitosan mucoadhesive, and mannitol and sucrose (or other sugars such as dextrose, lactose, trehalose and glycerol) as bulking agents and to provide proper flow characteristics. The formulation may comprise about 7.0 mg (25 to 90% w/w range) chitosan, about 1.5 mg mannitol (0 to 50% w/w range), about 1.5 mg sucrose (0 to 50% w/w range), about 25 µg MPL (0.1 to 5% w/w range), and about 100 µg norovirus antigen (0.05 to 5% w/w range).

Continuing with the norovirus vaccine formulation described above, the norovirus antigen may be present in the vaccine at a concentration of from about 0.01% (w/w) to about 80% (w/w). In some embodiments, norovirus antigens can be formulated at dosages of about 5 µg, about 15 µg, and about 50 µg per 10 mg dry powder formulation (0.025, 0.075 and 0.25% w/w) for administration into both nostrils or about 10 µg, about 30 µg, and about 100 µg (0.1, 0.3 and 1.0% w/w) for administration into one nostril. The formulation may be given in one or both nostrils during each administration. There may be a booster administration 1 to 12 weeks after the first administration to improve the immune response. The content of the norovirus antigens in the vaccine and antigenic formulations may be in the range of 1 µg to 100 mg, preferably in the range 1-500 µg, more preferably 5-200 µg, most typically in the range 10-100 µg. Total norovirus antigen administered at each dose may be about 10 µg, about 30 µg, or about 100 µg in a total of 20 mg dry powder when administered to both nostrils, or 10 mg dry powder when administered to one nostril. Dry powder characteristics are such that less than 10% of the particles are less than 10 µm in diameter. Mean particle sizes range from 10 to 500 µm in diameter.

In some embodiments, the vaccine composition is a lyophilized powder and reconstituted to an aqueous formulation. The invention hence encompasses methods of making purified norovirus compositions comprising (a) preparing a pre-lyophilization solution comprising norovirus antigen, sucrose, and chitosan, wherein the ratios of sucrose to chitosan are from about 0:1 to about 10:1; (b) freezing the solution; and (c) lyophilizing the frozen solution for 30-72 hours, wherein the final lyophilized product contains a percentage of said norovirus antigen in aggregated form. The lyophilization may occur at ambient temperature, reduced temperature, or proceed in cycles at various temperatures. For illustration purposes only, lyophilization may occur over a series of steps, for instance a cycle starting at −69° C., gradually adjusting to −24° C. over 3 hours, then retaining this temperature for 18 hours, then gradually adjusting to −16° C. over 1 hour, then retaining this temperature for 6 hours, then gradually adjusting to +34° C. over 3 hours, and finally retaining this temperature over 9 hours. In one embodiment, the pre-lyophilization solution further comprises a bulking agent. In another embodiment, said bulking agent is mannitol.

Appropriate ratios of sucrose and chitosan to yield desired percentages of aggregation can be determined by the following guidelines. A pre-lyophilization mixture containing mass ratios of sucrose to chitosan in a range from about 2:1 to about 10:1 will yield a range of about 50% to 100% intact viral antigen (i.e. 0% to 50% aggregated antigen) post-lyophilization depending on pre-lyophilization solution concentrations. Mass ratios of 0:1 sucrose to chitosan will produce less than 30% of intact norovirus antigen (i.e. greater than 70% aggregated antigen). Omission of both sucrose and chitosan and use of only a bulking agent, such as mannitol, will produce less than 10% intact antigen (i.e. greater than 90% aggregated antigen depending on pre-lyophilization solution concentrations). Using these guidelines, the skilled artisan could adjust the sucrose to chitosan mass ratios and concentrations in the pre-lyophilization mixture to obtain the desired amount of aggregation necessary to produce an optimal immune response.

The vaccines may be administered in a manner compatible with the dosage formulation, and in such amount as will be therapeutically effective and immunogenic. Further, various methods of achieving adjuvant effect for vaccines are known and may be used in conjunction with the VLPs disclosed herein.

A variety of host-expression vector systems may be utilized to express the VLP polypeptides. Such host-expression systems represent vehicles by which the VLP polypeptides may be produced to generate VLPs.

In mammalian host cells, a number of viral-based expression systems may be utilized. In addition, a host cell strain may be chosen which modulates the expression of the inserted sequences, or modifies and processes the gene product in the specific fashion desired. Such modifications of protein products may be important for the generation of the VLP or function of a VLP polypeptide or additional polypeptide such as an adjuvant or additional antigen. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

Certain aspects of the present invention include additional antigens associated with the VLP preparations, and can be any substance capable of eliciting an immune response. In some embodiments, the antigen may be any allergen. Allergens include but are not limited to cells, cell extracts, proteins, polypeptides, peptides, polysaccharides, polysaccharide conjugates, peptide and non-peptide mimics of polysaccharides and other molecules, small molecules, lipids, glycolipids, and carbohydrates.

This invention will be better understood by reference to the following non-limiting Examples. As used in this specification, the singular forms "a," "an" and "the" include plural referents unless the context clearly dictates otherwise. Where methods and/or schematics described above indicate certain events and/or flow patterns occurring in certain order, the ordering of certain events and/or flow patterns may be modified. For example, processing of VLPs by low pH treatment may be carried out for any process intermediate generated during the vaccine manufacturing process including, but not limited to, bulk production cultures, clarified production cultures, chromatography elution fractions, chromatography flow-through/wash fractions, ultrafiltration/diafiltration retentate fractions, and/or process fraction filtrates.

Additionally certain events may be performed concurrently in parallel processes when possible, as well as performed sequentially.

Examples

Sf9 Culture

Routine culture of Sf9 insect cells was performed in flasks at 27° C. and ambient air saturation. Sf9 cells were cultured over multiple passages for baculovirus expansion and production of VLPs. Routine counting of Sf9 cultures was carried out using an automated cell counter (T4 Cellometer, Nexcelom Bioscience).

Recombinant Baculovirus

Recombinant baculovirus was generated by co-transfecting transfer vector and linear baculovirus DNA into adherent Sf9 insect cells using Cellfectin according to the manufacturer's instructions, followed by plaque purification and additional rounds of baculovirus expansion. Recombinant baculovirus was then harvested as a supernatant fraction obtained by low-speed centrifugation. The resulting recombinant baculovirus was adjusted to 10% DMSO final (v/v), alliquoted and stored at −80° C. Expansion of frozen baculovirus for VLP production was performed as outlined above.

VLP Production

Production of norovirus VLPs was carried out using disposable Wave bioreactors. For bioreactor production, Sf-900 II serum-free media was aseptically transferred to the Wave bioreactor and cultures were inoculated. Once an appropriate cell density had been reached, recombinant baculovirus was aseptically added to bioreactor cultures and expression cultures are incubated under conditions outlined above. Bioreactor cultures were typically harvested 4-6 days post-infection based on viable cell density.

In addition to norovirus VLPs, production cultures may be generated by infection with recombinant baculovirus containing a sapovirus VP1 subunit. Alternatively, production cultures may be generated by infection with recombinant baculovirus containing a norovirus VP1 subunit that has been engineered to contain foreign amino acids and/or antigens in surface exposed loop regions (chimeric norovirus VLPs).

Bioreactor Harvest

For harvest, bioreactor cultures were adjusted to pH-3.0 by addition of HCl and then incubated for 2 h at ambient temperature with stirring. Cultures were then adjusted to pH-5.0 (Norwalk) or pH-6.0 (Consensus) by addition of imidazole and then clarified by low-speed centrifugation. Final clarification of the bioreactor was carried out by filtration of the post-centrifuge supernatant. The resulting harvest material (conditioned media) was stored at ambient room temperature for ≤24 h or stored at 4° C. for ≤1 week prior to the next unit operation.

For harvest of bulk production cultures containing sapovirus or chimeric norovirus VLPs, studies will be conducted evaluating contaminant removal and VLP recovery following treatment at pH-2.5 for time periods ranging from 30 min to 48 h. Conditions that demonstrate the most favorable recovery of structurally-intact VLP and removal of process contaminants will be used for scale-up processing. A listing of engineered VLPs, including chimeric variants, suitable for this purpose may be generally found in PCT application serial no. PCT/US2011/022094 filed Jan. 21, 2011, titled "Targeted Heterologous Antigen Presentation on Calicivirus Virus-Like Particles", and in U.S. utility application Ser. No. 13/023,363 filed Aug. 10, 2009, titled "Virus-Like Particles Comprising Composite Capsid Amino Acid Sequences for Enhanced Cross Reactivity", the disclosures of which is incorporated by reference in their entirety.

Cation-Exchange Capture Chromatography

Cation-exchange (CE) capture chromatography of norovirus VLPs was carried out using a Sartobind S capsule. For purification, the capsule was equilibrated with Acetate (pH-5.0) and conditioned media (≤1.5 g VLP total) was loaded. The capsule was washed then with acetate (pH-5.0) until the flow-through absorption at 280 nm ($A_{280}$) was <200 mAU. The capsule was next saturated with acetate (pH-5.0), 1% Triton X-100, 0.2% tributyl phosphate, and washed. Following this on-column solvent/detergent treatment, the capsule was washed with acetate (pH-5.0) at 100 mL/min until $A_{280}$<50 mAU. The elution of norovirus VLPs was carried out with acetate (pH-5.0) and NaCl. The VLP elution fraction was collected into disposable bottles or bioprocess bags.

Purification of Consensus VLPs by cation-exchange chromatography was carried out as described above, with the exception that citrate (pH-6.0) was used in place of acetate (pH-5.0) for all process buffers.

Hydroxyapatite (HA) Capture Chromatography

Hydroxyapatite (HA) capture chromatography of Norwalk VLPs was carried out using a 250 mL bed volume CHT ceramic hydroxyapatite column (BioRad). For purification, the capsule was equilibrated with MES (pH-6.0) and conditioned media (≤250 mg VLP total) was loaded. The capsule was washed then with MES (pH-6.0) until the flow-through absorption at 280 nm ($A_{280}$) was <200 mAU. The capsule was next saturated with MES (pH-6.0), 1% Triton X-100, 0.2% tributyl phosphate, and washed. Following this on-column solvent/detergent treatment, the capsule was washed with MES (pH-6.0) at 70 mL/min until $A_{280}$<50 mAU. The elution of norovirus VLPs was carried out by washing with 100 mM sodium phosphate (pH-6.8) and VLP elution with 400 mM sodium phosphate (pH-6.8). The VLP elution fraction was collected into disposable bottles or bioprocess bags.

For chromatographic of sapovirus or chimeric norovirus VLPs with on-column solvent/detergent treatment, studies will be conducted evaluating buffer conditions (pH and ionic strength) that allow efficient binding and elution of VLPs from chromatographic matrices that include, but are not limited to, a cation exchange column, a hydroxyapatite column, a hydrophobic interaction column, a size exclusion column, an anion exchange column, a mixed mode column, or an affinity column. For conditions that demonstrate the most favorable recovery of structurally-intact VLP and removal of process contaminants, VLP processing (including solvent/detergent treatment) will be conducted in a manner analogous to that outlined above.

VLP Characterization

Following purification, norovirus VLPs were analyzed for purity by a panel of analytical methods. SDS-PAGE analysis was carried out using NuPAGE gradient gels. The resulting PAGE gels were stained with Imperial Protein Stain or silver stained. Baculovirus inactivation was assessed by standard plaque assays for low pH-treatment of production cultures and on-column solvent/detergent treatment during a capture chromatography step.

Analysis of Norwalk VLP structural integrity was carried out by analysis of purified product using size-exclusion chromatography (SEC) and transmission electron microscopy (EM). For SEC, purified Norwalk VLPs were diluted and analyzed on a Superose 6 column. For EM analysis, VLPs were diluted in L-histidine (pH-6.5), sodium chloride, spotted on copper mesh grids and stained with 2% uranyl acetate.

Results

Bioreactor production—To develop a scalable method for production of VLPs, Sf9 cultures were grown in Wave bioreactors for infection with recombinant baculovirus using techniques generally known in the art.

Bioreactor harvest—Following production of norovirus VLPs, bioreactor cultures contain high levels of viable baculovirus (~$10^7$-$10^8$ pfu/mL) that must be inactivated and cleared during VLP manufacturing. Studies were carried out to determine if low pH-treatment of production cultures represented a viable step during harvest. As shown in Table 1, high-level baculovirus (AcNPV) inactivation (>5 $\log_{10}$ for the Norwalk VLP process and >4 $\log_{10}$ for the Consensus VLP process) was achieved in studies where production cultures were incubated at pH<3.5 for 1 h at room temperature. Table 1 also demonstrates that high-level retrovirus (A-MLuV) inactivation (>7 $\log_{10}$ for the Norwalk VLP process and >6 $\log_{10}$ for the Consensus VLP process) was achieved. In contrast, analysis of production cultures by SDS-PAGE and size-exclusion chromatography demonstrated that both Norwalk and Consensus VLPs remained soluble and structurally intact following low pH treatment of production culture. During production, a N-terminal proteolytic cleavage is commonly observed in the norovirus VP1 subunit. In addition to clearance of significant levels of Sf9 host cell protein, demonstrates the selective removal of VLPs containing truncated VP1 by low pH treatment of bulk cultures (FIGS. 1A and 1B).

TABLE 1

Inactivation of enveloped viruses by low pH treatment of Norwalk and Consensus bulk production cultures

| Process step | Norwalk VLP process ($\log_{10}$ reduction) | | Consensus VLP process ($\log_{10}$ reduction) | |
| --- | --- | --- | --- | --- |
| | A-MuLV | AcNPV | A-MuLV | AcNPV |
| Low pH treatment | >7.79 | 5.55 | >6.37 | 4.47 |

Based on the above findings, a harvest strategy has been developed by low pH-treatment and primary clarification by low-speed centrifugation. To further protect the downstream capture step, the resulting low-speed supernatant/filtrate fraction is passed through a PES capsule filter and then into a sterile bioprocess bag containing a capsule filter. This harvest strategy provides efficient recovery of norovirus VLPs that are stable in the resulting conditioned media under the described storage conditions and generates a relatively pure VLP fraction for downstream processing.

Downstream processing—For downstream processing, emphasis has been placed on orthogonal purification, methods that are well-suited for scale up cGMP manufacturing. The following procedures were designed to process VLPs from the starting conditioned media.

Cation-exchange chromatography—Membrane-based chromatography has found utility for purification of large macromolecular complexes due to efficient mass transfer in the large diameter (~1 μm) membrane pores. Sartobind S cation-exchange membranes efficiently bind norovirus VLPs when compared with conventional, bead-based chromatography matrices have been used for capture and purification of VLPs from conditioned media (FIG. 2A). To increase baculovirus inactivation during norovirus VLP downstream processing, an on-column solvent/detergent treatment step using equilibration buffer containing 1% Triton X-100, tributyl phosphate has been incorporated into the capture step. Following a capsule wash to remove the solvent/detergent buffer, norovirus VLPs are eluted with a step gradient of equilibration buffer containing sodium chloride. The current processing scheme specifies a maximum of 1.5 g norovirus VLP in Conditioned Media loaded on the Sartobind S 10" capsule. As shown in Table 2 high-level baculovirus (AcNPV) inactivation (>4 $\log_{10}$ for the Norwalk VLP process and >4 $\log_{10}$ for the Consensus VLP process) was achieved. Tables 2 also demonstrates that high-level retrovirus (A-MLuV) inactivation (>71 $\log_{10}$ for the Norwalk VLP process and >6 $\log_{10}$ for the Consensus VLP process) was achieved. It was further observed that numerical addition of the purification values listed in Tables 1 and 2 were an accurate measure of inactivation of enveloped viruses when both low pH treatment and on-column solvent/detergent treatment were employed.

TABLE 2

Inactivation of enveloped viruses by cation-exchange chromatography with on-column solvent/detergent treatment

| Process step | Norwalk VLP process ($\log_{10}$ reduction) | | Consensus VLP process ($\log_{10}$ reduction) | |
| --- | --- | --- | --- | --- |
| | A-MuLV | AcNPV | A-MuLV | AcNPV |
| Cation exchange (S/D treatment) | >7.15 | >4.48 | >6.96 | >4.96 |

Similar to cation-exchange chromatography, hydroxyapatite capture chromatography with on-column solvent/detergent treatment has also been shown effective for processing of norovirus VLPs (FIG. 2B).

Figure 3B:
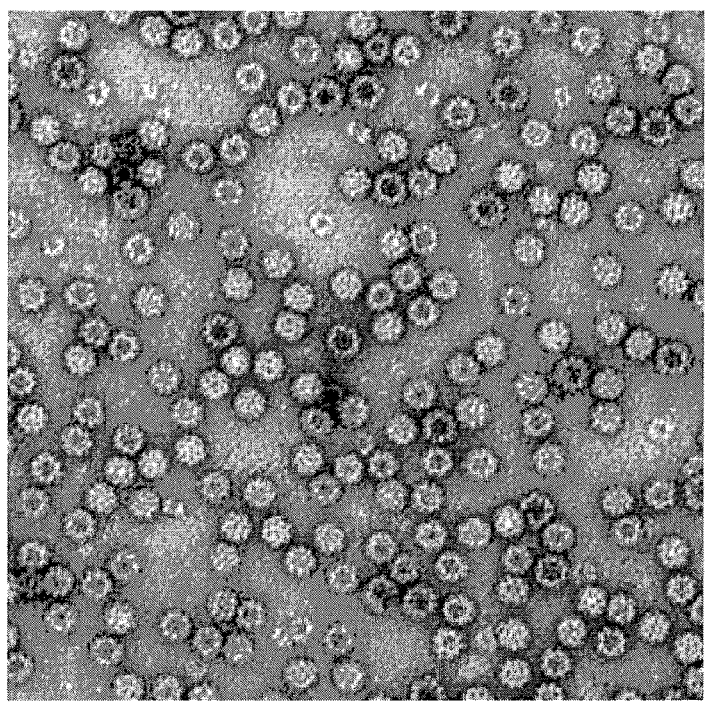
FIG. 3B, illustrating analysis of VLP integrity, is a transmission electron micrograph demonstrating ~30-40 nm particles anticipated of T3 icosohedral VLPs.
Figure 3A:
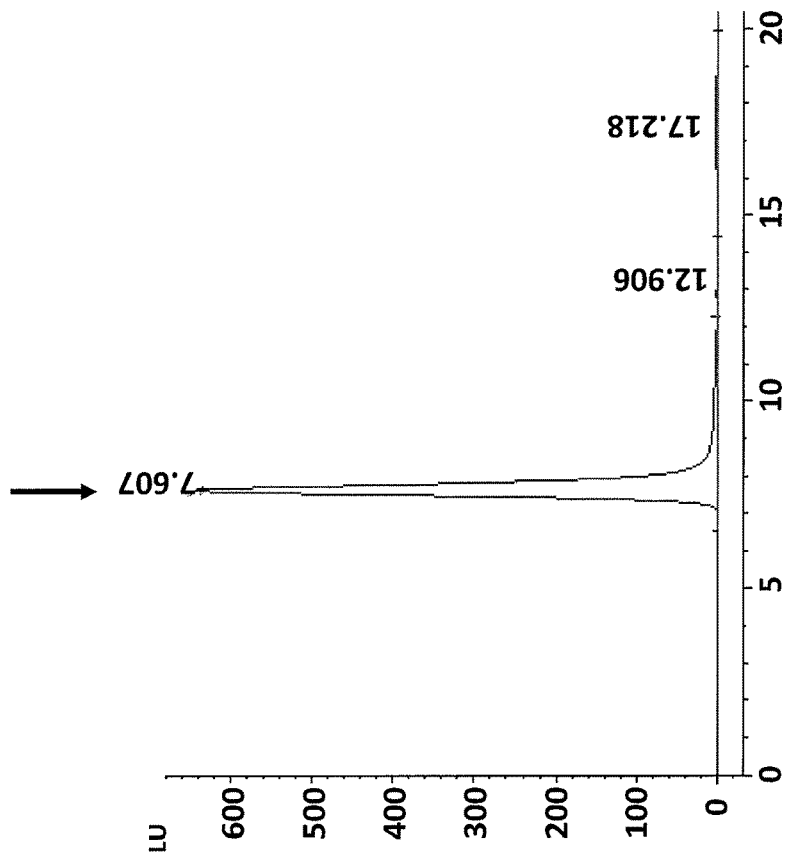
FIG. 3A, illustrating analysis of VLP integrity, is an analytical size-exclusion chromatogram where the chromatogram demonstrates a 7.4 minute peak consistent with assembled particles.

Characterization of purified norovirus VLPs—To evaluate the assembly state of VLPs following production and downstream processing using multi-step chromatographic processes, purified VLPs were analyzed by size-exclusion chromatography (SEC) and transmission electron microscopy (EM). When analyzed by SEC under the described conditions, Norwalk and Consensus VLPs show a retention time of approximately 7.2-7.6 minutes is consistent with a purified product having a molecular weight of several million Daltons (FIG. 3A) Since disassembled VP1 capsid protein elutes with a retention time of approximately 15 minutes, these results confirm that the majority of the capsid protein is incorporated in an assembled VLP. Analysis of purified material by transmission indicates predominantly uniform particles of ~35-40 nm for both Norwalk and Consensus VLPs, consistent with a T3 icosahedral assemblage of VP1 capsid monomers (FIG. 3B).

Viral Inactivation/Clearance by Solvent/Detergent Treatment.

Consensus VLP conditioned media was spiked with model viruses and processed by cation exchange chromatography with and without on-column solvent/detergent treatment. As shown in Table 3, minimal reduction of the model viruses was observed by the CE step alone while including the on-column solvent/detergent treatment provided high-level clearance/inactivation.

TABLE 3

Viral inactivation/clearance by solvent/detergent treatment I

| Consensus VLP process step | Model Virus ($\log_{10}$ reduction) | |
|---|---|---|
| | A-MuLV[1] | AcNPV[2] |
| Cation-exchange | 1.18 | 0.59 |
| CCation-exchange (S/D treatment) | >6.96 | >4.96 |

[1]Amphotropic Murine Leukemia virus.
[2]Baculovirus.

Viral Inactivation/Clearance by Low pH and Solvent/Detergent Treatment.

Following production of norovirus VLPs in Sf9 insect cells, bioreactor production cultures contain high levels of live baculovirus (~$10^8$ pfu/mL) following harvest by conventional methods (low speed centrifugation and filtration). Table 4 shows that while low pH treatment alone does not completely inactivate baculovirus at levels found in production cultures. In contrast, the level of baculovirus inactivation by a combination of low pH and solvent/detergent treatment exceeds the ~10 pfu/mL in production cultures.

TABLE 4

Viral inactivation/clearance by low pH and solvent/detergent treatment
Baculovirus reduction ($\log_{10}$)

| Process step | Norwalk VLP | Consensus VLP |
|---|---|---|
| Low pH treatment | 5.55 | 4.47 |
| Cation-exchange (S/D treatment) | >4.48 | >4.96 |
| Cumulative | >10.03 | >9.43 |

Removal of VP1 Proteolytic Fragments by Low pH Treatment

During production in the baculovirus expression system, the Consensus VP1 subunit can undergo proteolytic cleavage resulting in an N-terminal truncation production for a certain fraction of the expressed material. This proteolytic fragment assembles into VLPs and co-purifies with VLPs composed of the full-length VP1 subunit during downstream processing. During development studies, it was discovered that low pH treatment of bulk bioreactor production cultures selectively removed the population of VLPs containing the N-terminal truncation product providing more homogenous material for downstream processing.

Following downstream processing, analysis of Consensus VLP Drug Substance by silver stain SDS-PAGE and densitometry demonstrated significant levels of the VP1 N-terminal truncation product for VLPs purified from bioreactor cultures that were not pH treated at harvest (Table 5). In contrast, VLPs purified from pH-treated bioreactor cultures were composed exclusively of the full-length VP1 subunit.

TABLE 5

Removal of the Consensus VP1 proteolytic fragment by low pH treatment.

| Bioreactor harvest method | Full length VP1 (%) | N-terminal truncation (%) |
|---|---|---|
| No pH treatment[1] | 77 ± 14 | 23 ± 13 |
| Low pH treatment[1] | 100 ± 0 | 0 ± 0 |

[1]Results shown for five individual Consensus VLP lots.

Host Cell Protein Clearance by On-Column Solvent/Detergent Treatment

Following harvest of bioreactor production cultures, Norwalk and Consensus VLPs are processed by cation-exchange (CE) chromatography with on-column solvent/detergent treatment. The VLP and Sf9 host cell protein (HCP) content were evaluated for both bioreactor harvest material (CE load) and the cation-exchange elution fraction (CE elution). For these studies, VLP content was determined by size-exclusion chromatography and HCP content was determined using a commercially-available ELISA kit (Cygnus Technologies, Cat: F020). Table 6 shows data averaged over multiple VLP lots for the HCP content of process fractions, and demonstrates significant HCP reduction by the CE step as determined by the assays described above.

TABLE 6

Purification of Norwalk and Consensus VLPs by on-column solvent/detergent treatment

| Process fraction | VLP content | HCP content | HCP content relative to VLP (%) |
|---|---|---|---|
| Norwalk VLP | | | |
| CE load | 1245 | 1258 | 101 |
| CE elution | 804 | 71 | 9 |
| Consensus VLP | | | |
| CE load | 1580 | 1706 | 108 |
| CE elution | 1281 | 15 | 1 |

Figures 4A, 4B:
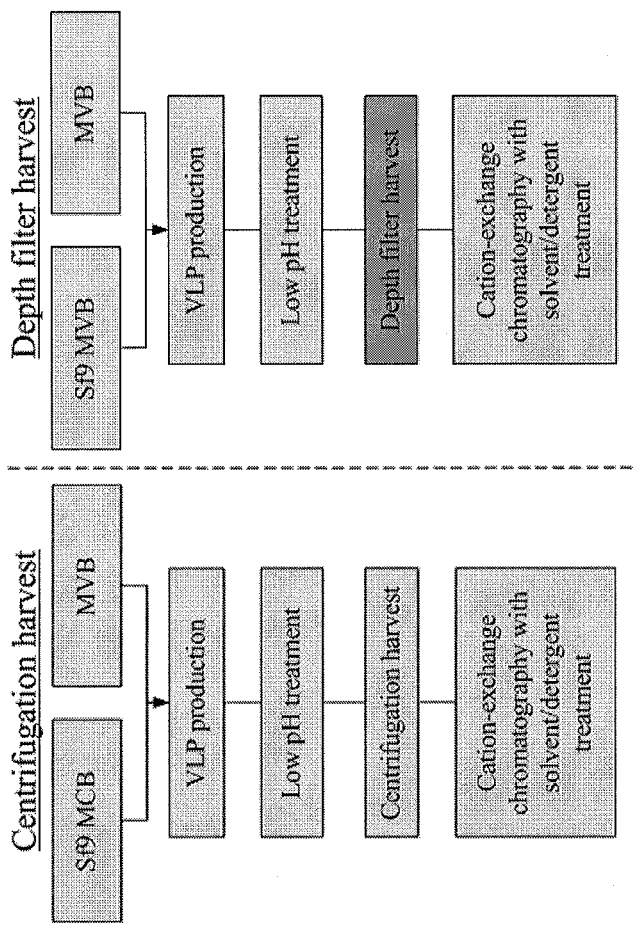
FIG. 4A, illustrating a flow diagram for VLP production and harvest via centrifugation.
FIG. 4B, illustrating a flow diagram for VLP production and harvest via depth filtration.

Harvest of Norwalk and Consensus VLP Bioreactor Production Cultures by Low pH Treatment and Depth Filtration For current manufacturing of Norwalk and Consensus VLPs, bioreactor production cultures are harvested by low pH treatment and clarification by centrifugation/filtration. The low pH treatment step of the current harvest procedure is used for virus inactivation and removal of process contaminants, while centrifugation is used for primary clarification of production cultures. While centrifugation represents a well-established and scalable method for bioreactor clarification (see FIG. 4A), the alternate use of depth filtration for primary clarification (see FIG. 4B) offers a number of advantages including ease of operation and availability of disposable materials that eliminate the requirement for cleaning validation.

In order to further characterize and refine the harvest of bioreactor production cultures, development studies were carried out to: 1) evaluate clearance of baculovirus and host cell nucleic acid process contaminants; and 2) evaluate the use of diatomaceous earth depth filters for primary clarification. The studies outlined above are summarized in FIGS. 4A-4B, and were carried out as follows:

Norwalk and Consensus VLP production cultures were generated in shake flasks or stirred tank bioreactors.

Production cultures were harvested by: low-speed centrifugation and 0.2 µm filtration; low pH treatment followed by low-speed centrifugation and 0.2 µm filtration; low pH treatment followed by depth filtration and 0.2 µm filtration.

The nucleic acid content of process fractions was evaluated by qPCR and VLP recovery evaluated by size-exclusion chromatography.

For the studies shown in Table 7, the low pH treatment step at harvest results in significant clearance of nucleic acid contaminants for both Norwalk (12.7 to 47.4-fold reduction) and Consensus (2.9 to 3.0-fold reduction) VLP production cultures. In addition, primary clarification using a depth filter in the place of centrifugation increased the overall clearance of nucleic acid contaminants for both Norwalk (65.0 to 110.9-fold reduction) and Consensus (30.7 to 51.9-fold reduction) VLP production cultures.

TABLE 7

Nucleic acid clearance by low pH treatment and depth filtration

| Process fraction | Baculovirus nucleic acid (pg/mL) | Sf9 nucleic acid (pg/mL) |
|---|---|---|
| Norwalk VLP harvest | | |
| Starting culture[1] | 747.7 | 7420.0 |
| Low pH harvest[2] | 58.9 | 156.3 |
| Low pH/depth filter harvest[3] | 11.5 | 66.9 |
| Consensus VLP harvest | | |
| Starting culture[1] | $1.6 \times 10^5$ | $8.3 \times 10^5$ |
| Low pH harvest[2] | $5.3 \times 10^4$ | $2.9 \times 10^5$ |
| Low pH/depth filter harvest[3] | $5.2 \times 10^3$ | $1.6 \times 10^4$ |

[1]Harvest fraction clarified by centrifugation/0.2 µm filtration (no pH treatment).
[2]Harvest fraction following pH treatment and centrifugation/0.2 µm filtration.
[3]Harvest fraction following pH treatment and Millistak + D0HC depth filtration/0.2 µm filtration.

As shown in Table 8, capacities ranging from 155-390 L/m² and VLP recoveries of 73-101% were observed in harvest studies using a variety of depth filters. The favorable filter capacities and VLP recoveries observed makes such an approach appropriate for use scale-up manufacturing.

TABLE 8

Depth filter capacity and VLP recovery.

| Parameter | Depth filter | | | |
| | Zeta Plus BC25 10SP02A | Zeta Plus BC25 30SP02A2 | Sartoclear PB2 Cap | Millistak + D0HC |
|---|---|---|---|---|
| Norwalk VLP | | | | |
| Filter capacity (L/m²) | N/A | N/A | 179 | 163 |
| VLP recovery by depth filtration (%) | N/A | N/A | 98 | 101 |
| Consensus VLP | | | | |
| Filter capacity (L/m²) | 202 | 155 | 334 | 390 |
| VLP recovery by depth filtration (%) | 87 | 79 | 73 | 90 |

N/A—not available.

The invention claimed is:

1. A solution comprising a purified population of human norovirus VLPs, wherein the norovirus VLPs comprise at least genogroup II VLPs, wherein said solution contains no more than about 80% residual contaminating protein relative to VLP, and wherein said solution is generated by a process comprising:
   generating or obtaining a cell lysate, culture supernatant, or filtrate containing the norovirus VLPs, wherein said norovirus VLPs comprise at least a first subpopulation with full length VP1 subunit and a second subpopulation with truncated VP1 subunit of the norovirus VLPs;
   adjusting the pH of the lysate, supernatant or filtrate to a pH of less than about 5 to generate a pH-adjusted solution;
   removing the second subpopulation with truncated VP1 subunit of norovirus VLPs from the pH-adjusted solution using a filtration process to generate a filtered solution, wherein the filtered solution substantially retains the first subpopulation with full length VP1 subunit of norovirus VLPs;
   and
   wherein the solution comprises full length VP1 subunit of norovirus VLPs and is substantially free of norovirus VLPs with the truncated VP1 subunit, wherein the solution contains less than about 10% truncated VP1 subunit.

2. A vaccine comprising the norovirus VLPs prepared from the solution of claim 1.

3. The solution of claim 1, containing no more than about 35% residual contaminating nucleic acid relative to the lysate, supernatant or filtrate.

4. The solution of claim 1, wherein at least about 50% of the norovirus VLPs are recovered from the lysate, supernatant or filtrate.

5. The solution of claim 1, wherein the ratio of the norovirus VLPs to residual contaminating protein is increased at least about ten-fold as compared to the lysate, supernatant or filtrate.

6. The solution of claim 1, wherein the solution is suitable for use in a commercial process.

7. The solution of claim 1, wherein the process further comprises one or more of the following: centrifugation, precipitation, flocculation, settling, and filtration.

8. The solution of claim 6, wherein the commercial process has a processing volume of at least 20 liters.

9. The solution of claim 1, wherein the residual contaminating protein relative to VLP is measured by size exclusion chromatography and ELISA.

* * * * *

UNITED STATES PATENT AND TRADEMARK OFFICE
CERTIFICATE OF CORRECTION

PATENT NO. : 10,167,320 B2
APPLICATION NO. : 13/925449
DATED : January 1, 2019
INVENTOR(S) : Taylor Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this
Twenty-sixth Day of May, 2020

Andrei Iancu
*Director of the United States Patent and Trademark Office*